(12) United States Patent
Fischer et al.

(10) Patent No.: US 8,859,782 B2
(45) Date of Patent: Oct. 14, 2014

(54) PROCESS FOR THE PREPARATION OF 1-H-PYRROLIDINE-2,4-DIONE DERIVATIVES

(75) Inventors: Reiner Fischer, Monheim (DE); Thomas Himmler, Odenthal (DE)

(73) Assignee: Bayer CropScience AG, Monheim (DE)

( * ) Notice: Subject to any disclaimer, the term of this patent is extended or adjusted under 35 U.S.C. 154(b) by 0 days.

(21) Appl. No.: 13/358,348

(22) Filed: Jan. 25, 2012

(65) Prior Publication Data
US 2012/0190865 A1 Jul. 26, 2012

Related U.S. Application Data

(60) Provisional application No. 61/435,910, filed on Jan. 25, 2011.

(30) Foreign Application Priority Data

Jan. 25, 2011 (EP) .................................... 11152069

(51) Int. Cl.
| | | |
|---|---|---|
| C07D 209/54 | (2006.01) | |
| C07D 207/36 | (2006.01) | |
| C07D 491/107 | (2006.01) | |
| C07D 491/113 | (2006.01) | |

(52) U.S. Cl.
CPC ............ *C07D 207/36* (2013.01); *C07D 209/54* (2013.01); *C07D 491/107* (2013.01); *C07D 491/113* (2013.01)
USPC .......................................... 548/408; 514/409

(58) Field of Classification Search
CPC ...................................................... C07D 209/54
USPC ........................................... 548/408; 514/409
See application file for complete search history.

(56) References Cited

U.S. PATENT DOCUMENTS

| | | | |
|---|---|---|---|
| 5,258,527 A | 11/1993 | Krauskopf et al. | |
| 5,462,913 A | 10/1995 | Fischer et al. | |
| 5,504,057 A | 4/1996 | Fischer et al. | |
| 5,508,436 A | 4/1996 | Fischer et al. | |
| 5,567,671 A | 10/1996 | Fischer et al. | |
| 5,589,469 A | 12/1996 | Fischer et al. | |
| 5,622,917 A | 4/1997 | Fischer et al. | |
| 5,683,965 A | 11/1997 | Bachmann et al. | |
| 5,830,826 A | 11/1998 | Fischer et al. | |
| 6,114,374 A * | 9/2000 | Lieb et al. .................. | 514/424 |
| 6,133,296 A | 10/2000 | Lieb et al. | |
| 6,200,932 B1 | 3/2001 | Fischer et al. | |
| 6,288,102 B1 | 9/2001 | Hagemann et al. | |
| 6,589,976 B1 | 7/2003 | Fischer et al. | |
| 6,861,391 B1 | 3/2005 | Fischer et al. | |
| 2001/0004629 A1 | 6/2001 | Lieb et al. | |
| 2002/0010204 A1 | 1/2002 | Lieb et al. | |
| 2002/0022575 A1 | 2/2002 | Fischer et al. | |
| 2003/0045432 A1 | 3/2003 | Fischer et al. | |
| 2003/0096806 A1 | 5/2003 | Lieb et al. | |
| 2003/0171219 A1 | 9/2003 | Lieb et al. | |
| 2003/0216260 A1 | 11/2003 | Ruther et al. | |
| 2004/0019061 A1 | 1/2004 | Fischer et al. | |
| 2004/0102327 A1 | 5/2004 | Hagemann et al. | |
| 2004/0127365 A1 | 7/2004 | Lieb et al. | |
| 2005/0054535 A1 | 3/2005 | Fischer et al. | |
| 2005/0164885 A1 | 7/2005 | Lieb et al. | |
| 2005/0187110 A1 | 8/2005 | Maetzke et al. | |
| 2006/0160847 A1 | 7/2006 | Fischer et al. | |
| 2006/0166829 A1 | 7/2006 | Fischer et al. | |
| 2007/0015664 A1 | 1/2007 | Fischer et al. | |
| 2007/0032539 A1 | 2/2007 | Himmler | |
| 2007/0043219 A1 | 2/2007 | Himmler et al. | |
| 2007/0129252 A1 | 6/2007 | Fischer et al. | |
| 2007/0225167 A1 | 9/2007 | Fischer et al. | |
| 2007/0225170 A1 | 9/2007 | Fischer et al. | |
| 2007/0244007 A1 | 10/2007 | Fischer et al. | |
| 2007/0275858 A1 | 11/2007 | Fischer et al. | |
| 2007/0298968 A1 | 12/2007 | Bretschneider et al. | |
| 2007/0298969 A1 | 12/2007 | Fischer et al. | |
| 2008/0081807 A1 | 4/2008 | Lieb et al. | |
| 2008/0220973 A1 | 9/2008 | Fischer et al. | |
| 2008/0305955 A1 | 12/2008 | Bretschneider et al. | |
| 2008/0318776 A1 | 12/2008 | Fischer et al. | |
| 2009/0029858 A1 | 1/2009 | Fischer et al. | |
| 2009/0215624 A1 | 8/2009 | Fischer et al. | |
| 2009/0239906 A1 | 9/2009 | Fischer et al. | |
| 2009/0298828 A1 | 12/2009 | Fischer et al. | |
| 2009/0305891 A1 | 12/2009 | Fischer et al. | |
| 2010/0004127 A1 | 1/2010 | Fischer et al. | |
| 2010/0009850 A1 | 1/2010 | Fischer et al. | |
| 2010/0261608 A1 | 10/2010 | Fischer et al. | |

(Continued)

FOREIGN PATENT DOCUMENTS

| | | |
|---|---|---|
| DE | 44 09 044 A1 | 2/1995 |
| DE | 195 15 690 A1 | 10/1996 |

(Continued)

OTHER PUBLICATIONS

Altman et al. (J. Am. Chem. Soc. 2008, 130, 9613-9620).*
Hama et al. (J. Am. Chem. Soc. 2006, 128, 4976-4985).*
"Reaktionen von Carbonsäuren und Carbonsäurederivaten mit Basen," *Organikum*, p. 505, VEB Deutscher Verlag der Wissenschaften , Germany (1977).
Bhattacharya, B., "Isoquinoline Derivativs: Part XVIII-Formation of I-Alkyl-(or alkaryl or aryl)-3-methyl-7-chloro-(or 5-chloro)-isoquinolines," *Indian J. Chem.* 6:341-345, Council of Sientific & Industrial Research, India (1968).
Compagnon, P.L. and Miocque, M., "Addition Des Réactifs Nucléophiles Sur La Triple Liaison Nitrile," *Ann. Chim.* 14(5):11-27, Società Chimica Italiana, Italy (1970).
Edward, J.T., and Jitrangsri, C., "Stereochemistry of the Bucherer-Bergs and Strecker Reactions of 4-tert-Butylcyclohexanone," *Can. J. Chem.* 53:3339-3350, National Research Council, Canada (1975).
Fox, J.M., et al., "Highly Active and Selective Catalysts for the Formation of α-Aryl Ketones," *J. Am. Chem. Soc.* 122:1360-1370, American Chemical Society, United States (2000).
Harrison, H.R. et al., "Use of molecular sieves in the methyl esterification of carboxylic acids," *Chemistry and Industry* 1568, Society of Chemistry and Industry, England (1968).

(Continued)

*Primary Examiner* — Robert Havlin
(74) *Attorney, Agent, or Firm* — Sterne, Kessler, Goldstein & Fox P.L.L.C.

(57) ABSTRACT

The present invention relates to a novel process for the preparation of 1-H-pyrrolidine-2,4-dione derivatives and to novel intermediates and to a process for their preparation.

5 Claims, No Drawings

(56) References Cited

U.S. PATENT DOCUMENTS

| | | |
|---|---|---|
| 2010/0279873 A1 | 11/2010 | Fischer et al. |
| 2010/0311593 A1 | 12/2010 | Fischer et al. |
| 2011/0086762 A1 | 4/2011 | Fischer et al. |
| 2011/0130284 A1 | 6/2011 | Fischer et al. |
| 2011/0230346 A1 | 9/2011 | Fischer et al. |
| 2011/0230351 A1 | 9/2011 | Fischer et al. |
| 2011/0263424 A1 | 10/2011 | Bretschneider et al. |
| 2011/0306499 A1 | 12/2011 | Bretschneider et al. |
| 2012/0012833 A1 | 1/2012 | Shirasawa et al. |
| 2012/0015807 A1 | 1/2012 | Fischer et al. |

FOREIGN PATENT DOCUMENTS

| | | | |
|---|---|---|---|
| DE | 10 2005 059 892 A1 | | 6/2007 |
| DE | 10 2010 008 642 A1 | | 8/2011 |
| DE | 10 2010 008 643 A1 | | 8/2011 |
| WO | WO 03/059065 A1 | | 7/2003 |
| WO | WO 03/062244 A1 | | 7/2003 |
| WO | WO 2008/128058 A1 | | 10/2008 |
| WO | WO 2008/138551 A2 | | 11/2008 |
| WO | WO 2009/049851 A1 | | 4/2009 |
| WO | WO2010/052161 | * | 5/2010 |
| WO | WO 2010/052161 A2 | | 5/2010 |
| WO | WO 2010/063670 A1 | | 6/2010 |
| WO | WO 2011/067135 A1 | | 6/2011 |
| WO | WO 2011/067240 A1 | | 6/2011 |
| WO | WO 2011/098433 A1 | | 8/2011 |

OTHER PUBLICATIONS

Mizuno, H., et al., "Stereochemical Studies. VII. [1)] Thermal Rearrangement of α-Hydroxyimines to α-Aminoketones using optically Active Open Chain Compounds[2,3)]," *Chem. Pharm. Bull.* 19(2):227-246, Pharmaceutical Society of Japan, Japan (1971).

Munday, L., "Amino-acids of the Cyclohexane Series. Part I." *J. Chem. Soc.*:4372-4379, Journal of the Chemical Society, England (1961).

Noland, W.E., and Sundberg, R.J., "Structure of the 2:2 Condensation Product of Nitromethane and Cyclohexanone," *J. Org. Chem.* 28(11):3150-3165, American Chemical Society, United States (1963).

Satoh, S., and Esashi, Y., "In Vivo Formation of 1-Malonylaminocyclopropane-1-Carboxylic Acid and its Relationship to Ethylene Production in Cocklebur Seed Segments: A Tracer Study With 1-Amino-2-Ethylcyclopropane-1-Carboxylic Acid," *Phytochemistry* 23(8):1561-1565, Pergamon Press Ltd, England (1984).

Sonntag, N.O.V., "The Reactions of Aliphatic Acid Chlorides," *Chemical Reviews* 52(2):237-416, American Chemical Society, United States (1953).

Storgaard, M., et al., "Palladium-Catalyzed α-Arylation of Tetramic Acids," *J. Org. Chem.* 74:5032-5040, American Chemical Society, United States (2009).

International Search Report for International Application No. PCT/EP2012/050840, European Patent Office, The Hague, Netherlands, mailed on Apr. 4, 2012.

English language Abstract of German Patent Publication No. DE 10 2010 008 642 A1, European Patent Office, espacenet database—Worldwide (2011).

English language Abstract of German Patent Publication No. DE 10 2010 008 643 A1, European Patent Office, espacenet database—Worldwide (2011).

English language Abstract of International Patent Publication No. WO 2011/098433 A1, European Patent Office, espacenet database—Worldwide (2011).

Unverified English language translation of International Patent Publication No. WO 03/059065 A1.

Unverified English language Translation of German Patent Publication No. DE 10 2005 059 892 A1.

Unverified English language Translation of International Patent Publication No. WO 2008/138551 A2.

\* cited by examiner

PROCESS FOR THE PREPARATION OF 1-H-PYRROLIDINE-2,4-DIONE DERIVATIVES

This application claims priority to U.S. Provisional Application No. 61/435,910, filed on Jan. 25, 2011 and to European Application No. 11152069.8, filed on Jan. 25, 2011. The contents of both applications are incorporated by reference herein in their entireties.

The present invention relates to a novel, process for the preparation of 1-H-pyrrolidine-2,4-dione derivatives and to novel intermediates and to a process for their preparation.

1-H-Pyrrolidine-2,4-dione derivatives with acaricidal, insecticidal, fungicidal and herbicidal effect are known: EP-A-456 063, EP-A-521 334, EP-A-596 298, EP-A-613 884, EP-A-613 885, WO 95/01 971, WO 95/26 954, WO 95/20 572, EP-A-0 668 267, WO 96/25 395, WO 96/35 664, WO 97/01 535, WO 97/02 243, WO 97/36 868, WO 97/43275, WO 98/05638, WO 98/06721, WO 98/25928, WO 99/24437, WO 99/43649, WO 99/48869, WO 99/55673, WO 01/17972, WO 01/23354, WO 01/74770, WO 03/013249, WO 03/062244, WO 2004/007448, WO 2004/024 688, WO 04/065366, WO 04/080962, WO 04/111042, WO 05/044791, WO 05/044796, WO 05/048710, WO 05/049569, WO 05/066125, WO 05/092897, WO 06/000355, WO 06/029799, WO 06/056281, WO 06/056282, WO 06/089633, WO 07/048, 545, DEA 102 00505 9892, WO 07/073,856, WO 07/096, 058, WO 07/121,868, WO 07/140,881, WO 08/067,873, WO 08/067,910, WO 08/067,911, WO 08/138,551, WO 09/015,801, WO 09/039,975, WO 09/049,851, WO 09/115,262, WO 10/052,161, WO 10/102,758, WO 10/063,378, WO 10/063,670, WO 10/102,758, WO 2011/098443, WO 2011/098440, WO 11/067,135, WO 11/067, 240, EP Application number 11154805.3. Moreover, ketal-substituted 1-H-arylpyrrolidine-2,4-diones are known from WO 99/16748. With pharmaceutical effect are known WO 2011/098433, DE-A-102010008642, DE-A-102010008643 and DE Application number 102010008640.

Biphenyl-substituted 1H-pyrrolidinedione derivatives with fungicidal effect are also known (WO 03/059065).

These are compounds of the formula (I)

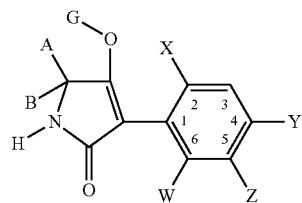

in which
W is hydrogen, halogen, alkyl, alkenyl, alkynyl, optionally substituted cycloalkyl, alkoxy, haloalkyl or haloalkoxy,
X is hydrogen, halogen, alkyl, alkenyl, alkynyl, optionally substituted cycloalkyl, alkoxy, haloalkyl, haloalkoxy or cyano,
Y and Z independently of one another are hydrogen, alkyl, alkenyl, alkynyl, halogen, cyano, optionally substituted cycloalkyl, alkoxy, haloalkyl, haloalkoxy or in each case optionally substituted aryl or hetaryl,
A is hydrogen, is in each case optionally halogen-substituted alkyl, alkenyl, alkoxyalkyl, alkylthioalkyl, saturated or unsaturated, optionally substituted cycloalkyl, in which optionally at least one ring atom is replaced by a heteroatom, or aryl, arylalkyl or hetaryl each of which is optionally substituted by halogen, alkyl, haloalkyl, alkoxy, haloalkoxy, cyano or nitro,
B is hydrogen, alkyl or alkoxyalkyl, or
A and B together with the carbon atom to which they are bonded are a saturated or unsaturated, unsubstituted or substituted cycle optionally containing at least one heteroatom,
G is hydrogen (a) or is one of the groups

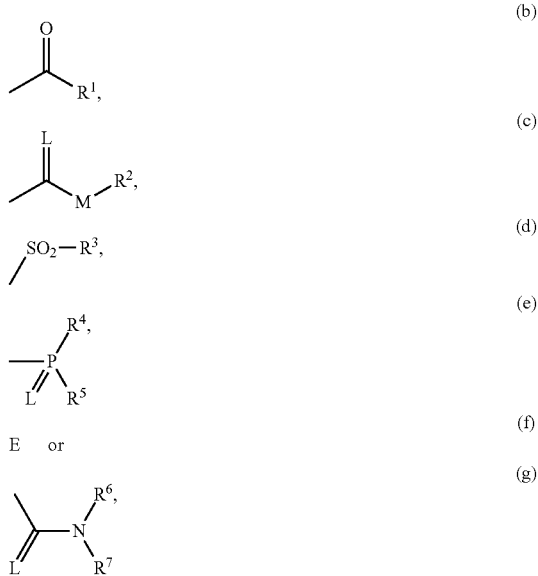

in which
E is a metal ion or an ammonium ion,
L is oxygen or sulphur,
M is oxygen or sulphur,
$R^1$ is alkyl, alkenyl, alkoxyalkyl, alkylthioalkyl or polyalkoxyalkyl each of which is optionally substituted by halogen or cyano, or is cycloalkyl or heterocyclyl each of which is optionally substituted by halogen, alkyl or alkoxy, or is in each case optionally substituted phenyl, phenylalkyl, hetaryl, phenoxyalkyl or hetaryloxyalkyl,
$R^2$ is alkyl, alkenyl, alkoxyalkyl or polyalkoxyalkyl each of which is optionally substituted by halogen or cyano, or is in each case optionally substituted cycloalkyl, phenyl or benzyl,
$R^3$, $R^4$ and $R^5$ independently of one another are in each case alkyl, alkoxy, alkylamino, dialkylamino, alkylthio, alkenylthio or cycloalkylthio optionally substituted by halogen, or are in each case optionally substituted phenyl, benzyl, phenoxy or phenylthio,
$R^6$ and $R^7$ independently of one another are hydrogen, are in each case alkyl, cycloalkyl, alkenyl, alkoxy, alkoxyalkyl optionally substituted by halogen or cyano, are in each case optionally substituted phenyl or benzyl, or together with the N atom to which they are bonded form a cycle which optionally contains oxygen or sulphur and is optionally substituted.

Depending inter alia on the nature of the substituents, the compounds of the formula (I) can be present as optical isomers or isomer mixtures of varying composition which, if desired, can be separated in the usual way. Both the pure isomers and the isomer mixtures, their preparation and use, and also compositions comprising these are provided by the present invention. For the sake of simplicity, however, reference is always made hereinbelow to compounds of the formula (I), although both the pure compounds and, if appropriate, also mixtures having different fractions of isomeric compounds are meant.

Taking into consideration the various meanings (a), (b), (c), (d), (e), (f) and (g) of the group G, the following main structures (I-a) to (I-g) arise,

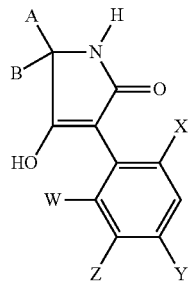
(I-a)

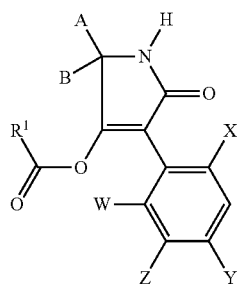
(I-b)

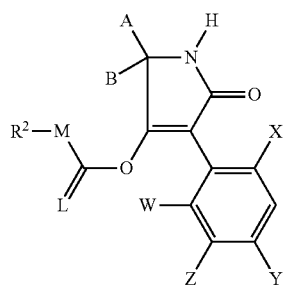
(I-c)

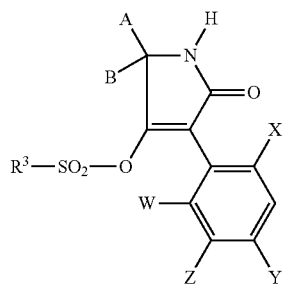
(I-d)

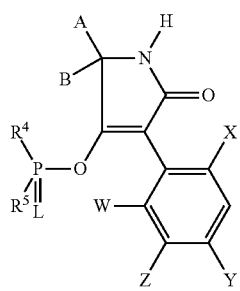
(I-e)

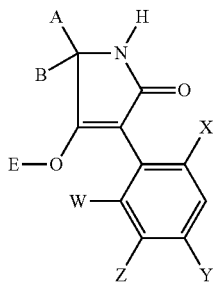
(I-f)

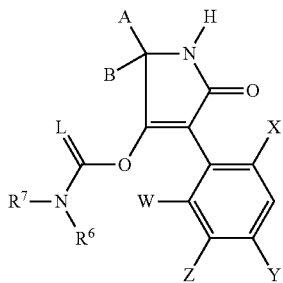
(I-g)

in which
A, B, E, L, M, W, X, Y, Z, $R^1$, $R^2$, $R^3$, $R^4$, $R^5$, $R^6$ and $R^7$ have the meanings given above.

Furthermore, it is already known that the compounds of the formula (I) are obtained by the processes described below:

(A*) Compounds of the formula (I-a)

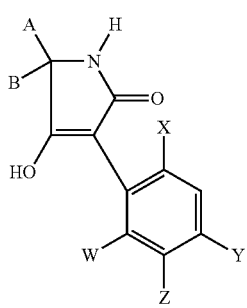
(I-a)

in which
A, B, W, X, Y and Z have the meanings given above, are obtained when
compounds of the formula (II)

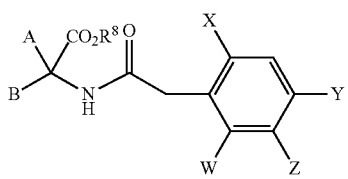
(II)

in which
A, B, W, X, Y and Z have the meanings given above, and
$R^8$ is alkyl,
are intramolecularly condensed in the presence of a diluent and in the presence of a base.

Moreover, it is known (B*) that the compounds of the formulae (I-b) shown above in which $R^1$, A, B, W, X, Y and Z have the meanings given above are obtained when compounds of the formulae (I-a) shown above in which A, B, W, X, Y and Z have the meanings given above, are in each case reacted α) with compounds of the formula (III)

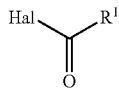   (III)

in which
$R^1$ has the meaning given above and
Hal is halogen (in particular chlorine or bromine)
or
β) with carboxylic anhydrides of the formula (IV)

$$R^1\text{—CO—O—CO—}R^1 \quad (IV)$$

in which
$R^1$ has the meaning given above,
optionally in the presence of a diluent and optionally in the presence of an acid binder;

(C*) that the compounds of the formulae (I-c) shown above in which $R^2$, A, B, M, W, X, Y and Z have the meanings given above and L is oxygen are obtained when compounds of the formulae (I-a) shown above in which A, B, W, X, Y and Z have the meanings given above, are in each case reacted with chloroformic acid esters or chloroformic acid thioesters of the formula (V)

$$R^2\text{-M-CO—Cl} \quad (V)$$

in which
$R^2$ and M have the meanings given above,
optionally in the presence of a diluent and optionally in the presence of an acid binder;

(D*) that compounds of the formulae (I-f) shown above in which E, A, B, W, X, Y and Z have the meanings given above are obtained when compounds of the formulae (I-a) in which A, B, W, X, Y and Z have the meanings given above, are in each case reacted
with metal compounds or amines of the formulae (XIII) or (XIV)

   (XIII)

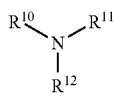   (XIV)

in which
Me is a mono- or divalent metal (preferably an alkali metal or alkaline earth metal such as lithium, sodium, potassium, magnesium or calcium),
t is the number 1 or 2 and
$R^{10}$, $R^{11}$, $R^{12}$, independently of one another, are hydrogen or alkyl (preferably $C_1$-$C_8$-alkyl), optionally in the presence of a diluent.

The compounds are generally defined by the formula (I). Preferred substituents and/or ranges of the radicals listed in the formulae mentioned above and below are explained hereinbelow:

W is preferably hydrogen, chlorine, bromine, $C_1$-$C_4$-alkyl, $C_2$-$C_4$-alkenyl, $C_2$-$C_4$-alkynyl, $C_3$-$C_6$-cycloalkyl optionally monosubstituted by methyl, ethyl, methoxy, fluorine, chlorine, trifluoromethyl or cyclopropyl, $C_1$-$C_4$-alkoxy, $C_1$-$C_2$-haloalkyl or $C_1$-$C_2$-haloalkoxy, X is preferably hydrogen, chlorine, bromine, iodine, $C_1$-$C_4$-alkyl, $C_2$-$C_4$-alkenyl, $C_2$-$C_4$-alkynyl, $C_3$-$C_6$-cycloalkyl optionally monosubstituted by methyl, ethyl, methoxy, fluorine, chlorine, trifluoromethyl or cyclopropyl, $C_1$-$C_4$-alkoxy, $C_1$-$C_4$-haloalkyl, $C_1$-$C_4$-haloalkoxy or cyano, Y and Z are preferably, independently of one another, hydrogen, cyano, fluorine, chlorine, bromine, iodine, $C_1$-$C_4$-alkyl, $C_2$-$C_4$-alkenyl, $C_2$-$C_4$-alkynyl, $C_3$-$C_6$-cycloalkyl optionally monosubstituted by methyl, ethyl, methoxy, fluorine, chlorine, trifluoromethyl or cyclopropyl, $C_1$-$C_6$-alkoxy, $C_1$-$C_4$-haloalkyl, $C_1$-$C_4$-haloalkoxy, or is one of the (Het)-aryl radicals,

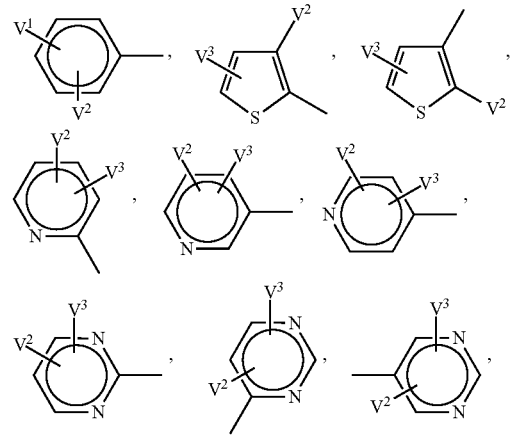

where in the case of (Het)-aryl only one of the radicals Y or Z may be (Het)-aryl, $V^1$ is preferably hydrogen, fluorine, chlorine, bromine, $C_1$-$C_6$-alkyl, $C_1$-$C_4$-alkoxy, $C_1$-$C_2$-haloalkyl, $C_1$-$C_2$-haloalkoxy, nitro, cyano or phenyl optionally mono- to disubstituted by fluorine, chlorine, bromine, $C_1$-$C_4$-alkyl, $C_1$-$C_4$-alkoxy, $C_1$-$C_2$-haloalkyl, $C_1$-$C_2$-haloalkoxy, nitro or cyano, $V^2$ and $V^3$ are preferably, independently of one another, hydrogen, fluorine, chlorine, bromine, $C_1$-$C_4$-alkyl, $C_1$-$C_4$-alkoxy, $C_1$-$C_2$-haloalkyl or $C_1$-$C_2$-haloalkoxy, A is preferably hydrogen, $C_1$-$C_6$-alkyl, $C_1$-$C_4$-alkoxy-$C_1$-$C_2$-alkyl, each of which is optionally mono- to trisubstituted by fluorine or chlorine, $C_3$-$C_6$-cycloalkyl which is optionally mono- to disubstituted by $C_1$-$C_2$-alkyl or $C_1$-$C_2$-alkoxy and which is optionally interrupted by an oxygen atom, or phenyl, pyridyl or benzyl each of which is optionally mono- to disubstituted by fluorine, chlorine, bromine, $C_1$-$C_4$-alkyl, $C_1$-$C_2$-haloalkyl, $C_1$-$C_4$-alkoxy, $C_1$-$C_2$-haloalkoxy, cyano or nitro, B is preferably hydrogen, $C_1$-$C_4$-alkyl or $C_1$-$C_2$-alkoxy-$C_1$-$C_2$-alkyl or A, B and the carbon atom to which they are bonded are preferably saturated or unsaturated $C_3$-$C_7$-cycloalkyl in which optionally one ring member is replaced by nitrogen, oxygen or sulphur and which is optionally mono- to disubstituted by halogen, $C_1$-$C_6$-alkyl, $C_1$-$C_4$-alkoxy-$C_1$-$C_2$-alkyl, trifluoromethyl, $C_1$-$C_6$-alkoxy, $C_3$-$C_6$-alkenyloxy, trifluoroethoxy, $C_1$-$C_3$-alkoxy-$C_1$-$C_3$-alkoxy or $C_3$-$C_6$-cycloalkylmethoxy, where the aforementioned radicals (with the exception of halogen and trifluoromethyl) are also suitable as N substituents, or A, B and the carbon atom to which they are bonded are preferably $C_5$-$C_6$-cycloalkyl which is substituted by an alkylenediyl group or by an alkylenedioxyl group or by an alkylenedithiol group which optionally contains with one or two non-directly adjacent oxygen or sulphur atoms and which is optionally substituted by methyl or ethyl, and which, with the carbon atom to which it is bonded, forms a further five- or six-membered ring, or A, B and the carbon atom to which they are bonded are preferably $C_3$-$C_6$-cycloalkyl or $C_5$-$C_6$-cycloalkenyl in which two substituents, together with the carbon atoms to which they are bonded, are $C_2$-$C_4$-alkanediyl, $C_2$-$C_4$-alkenediyl or butadienediyl each of which is optionally substituted by $C_1$-$C_2$-alkyl or $C_1$-$C_2$-alkoxy, G is preferably hydrogen (a) or is one of the groups

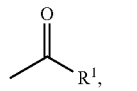
(b)

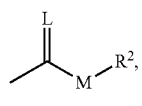
(c)

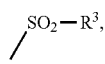
(d)

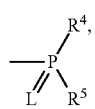
(e)

E, or
(f)

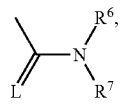
(g)

in which
E is a metal ion or an ammonium ion,
L is oxygen or sulphur and
M is oxygen or sulphur, $R^1$ is preferably $C_1$-$C_{16}$-alkyl, $C_2$-$C_{16}$-alkenyl, $C_1$-$C_6$-alkoxy-$C_1$-$C_4$-alkyl, $C_1$-$C_6$-alkylthio-$C_1$-$C_4$-alkyl or poly-$C_1$-$C_6$-alkoxy-$C_1$-$C_4$-alkyl each of which is optionally mono- to trisubstituted by fluorine or chlorine, or is $C_3$-$C_7$-cycloalkyl optionally mono- to disubstituted by fluorine, chlorine, $C_1$-$C_5$-alkyl or $C_1$-$C_5$-alkoxy, in which optionally one or two non-directly adjacent methylene groups are replaced by oxygen and/or sulphur,
is phenyl optionally mono- to trisubstituted by fluorine, chlorine, bromine, cyano, nitro, $C_1$-$C_4$-alkyl, $C_1$-$C_4$-alkoxy, $C_1$-$C_3$-haloalkyl, $C_1$-$C_3$-haloalkoxy, $C_1$-$C_4$-alkylthio or $C_1$-$C_4$-alkylsulphonyl,
is phenyl $C_1$-$C_4$-alkyl optionally mono- to disubstituted by fluorine, chlorine, bromine, $C_1$-$C_4$-alkyl, $C_1$-$C_4$-alkoxy, $C_1$-$C_3$-haloalkyl or $C_1$-$C_3$-haloalkoxy,
is pyrazolyl, thiazolyl, pyridyl, pyrimidyl, furanyl or thienyl each of which is optionally mono- to disubstituted by fluorine, chlorine, bromine or $C_1$-$C_4$-alkyl,
is phenoxy-$C_1$-$C_5$-alkyl optionally mono- to disubstituted by fluorine, chlorine, bromine or $C_1$-$C_4$-alkyl, or
is pyridyloxy-$C_1$-$C_5$-alkyl, pyrimidyloxy-$C_1$-$C_5$-alkyl or thiazolyloxy-$C_1$-$C_5$-alkyl each of which is optionally mono- to disubstituted by fluorine, chlorine, bromine, amino or $C_1$-$C_4$-alkyl, $R^2$ is preferably $C_1$-$C_{16}$-alkyl, $C_2$-$C_{16}$-alkenyl, $C_1$-$C_6$-alkoxy-$C_2$-$C_6$-alkyl or poly-$C_1$-$C_6$-alkoxy-$C_2$-$C_6$-alkyl each of which is optionally mono- to trisubstituted by fluorine or chlorine,
is $C_3$-$C_7$-cycloalkyl optionally mono- to disubstituted by fluorine, chlorine, $C_1$-$C_4$-alkyl or $C_1$-$C_4$-alkoxy or
is phenyl or benzyl each of which is optionally mono- to trisubstituted by fluorine, chlorine, bromine, cyano, nitro, $C_1$-$C_4$-alkyl, $C_1$-$C_3$-alkoxy, $C_1$-$C_3$-haloalkyl or $C_1$-$C_3$-haloalkoxy, $R^3$ is preferably $C_1$-$C_6$-alkyl optionally mono- to trisubstituted by fluorine or chlorine, or phenyl or benzyl each of which is optionally mono- to disubstituted by fluorine, chlorine, bromine, $C_1$-$C_4$-alkyl, $C_1$-$C_4$-alkoxy, $C_1$-$C_2$-haloalkoxy, $C_1$-$C_2$-haloalkyl, cyano or nitro, $R^4$ and $R^5$, independently of one another, are preferably $C_1$-$C_6$-alkyl, $C_1$-$C_6$-alkoxy, $C_1$-$C_6$-alkylamino, di($C_1$-$C_6$-alkyl)amino, $C_1$-$C_6$-alkylthio or $C_3$-$C_4$-alkenylthio each of which is optionally mono- to trisubstituted by fluorine or chlorine, or are phenyl, phenoxy or phenylthio each of which is optionally mono- to disubstituted by fluorine, chlorine, bromine, nitro, cyano, $C_1$-$C_3$-alkoxy, $C_1$-$C_3$-haloalkoxy, $C_1$-$C_3$-alkylthio, $C_1$-$C_3$-halo-alkylthio, $C_1$-$C_3$-alkyl, or $C_1$-$C_3$-haloalkyl, $R^6$ and $R^7$, independently of one another, are preferably hydrogen, $C_1$-$C_6$-alkyl, $C_3$-$C_6$-cycloalkyl, $C_1$-$C_6$-alkoxy, $C_3$-$C_6$-alkenyl or $C_1$-$C_6$-alkoxy-$C_2$-$C_6$-alkyl each of which is optionally mono- to trisubstituted by fluorine or chlorine, are phenyl or benzyl each of which is optionally mono- to trisubstituted by fluorine, chlorine, bromine, $C_1$-$C_5$-haloalkyl, $C_1$-$C_5$-alkyl or $C_1$-$C_5$-alkoxy, or together are a $C_3$-$C_6$-alkylene radical optionally substituted by $C_1$-$C_4$-alkyl in which optionally one methylene group is replaced by oxygen or sulphur.

In the radical definitions specified as preferred, halogen is fluorine, chlorine and bromine, in particular fluorine and chlorine.

W is particularly preferably hydrogen, chlorine, bromine, methyl, ethyl, methoxy, ethoxy or trifluoromethyl, X is particularly preferably hydrogen, chlorine, bromine, iodine, methyl, ethyl, propyl, cyclopropyl, methoxy, ethoxy, trifluoromethyl or trifluoromethoxy, Y and Z are particularly preferably, independently of one another, hydrogen, fluorine, chlorine, bromine, iodine, methyl, ethyl, cyclopropyl, methoxy, trifluoromethyl, trifluoromethoxy or a phenyl radical,

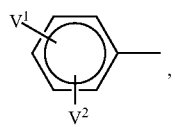

where in the case of phenyl, only one of the radicals Y or Z may be phenyl, $V^1$ is particularly preferably hydrogen, fluorine or chlorine,
$V^2$ is particularly preferably hydrogen, fluorine, chlorine, methyl, ethyl, n-propyl, isopropyl, methoxy, ethoxy or trifluoromethyl, A is particularly preferably hydrogen, $C_1$-$C_4$-alkyl or $C_1$-$C_2$-alkoxy-$C_1$-$C_2$-alkyl each of which is optionally mono- to trisubstituted by fluorine, is cyclopropyl, cyclopentyl or cyclohexyl, B is particularly preferably hydrogen, methyl or ethyl or A, B and the carbon atom to which they are bonded are particularly preferably saturated $C_5$-$C_6$-cycloalkyl in which optionally one ring member is replaced by nitrogen, oxygen or sulphur and which is optionally mono- or disubstituted by fluorine, chlorine, methyl, ethyl, methoxymethyl, ethoxymethyl, methoxyethyl, ethoxyethyl, trifluoromethyl, methoxy, ethoxy, propoxy, butoxy, methoxyethoxy, ethoxyethoxy, allyloxy, trifluoroethoxy or cyclopropylmethoxy, where the aforementioned radicals (with the exception of fluorine, chlorine and trifluoromethyl) are also suitable as N substituents, A, B and the carbon atom to which they are bonded are particularly preferably $C_6$-cycloalkyl which is optionally substituted by an alkylidenediyl group optionally interrupted by a with a oxygen atom, or by an alkylidenediyl group containing with two non-directly adjacent oxygen atoms, where a 5- or 6-ring ketal is formed and which may in each case be optionally mono- or disubstituted by methyl, or A, B and the carbon atom to which they are bonded are particularly preferably $C_5$-$C_6$-cycloalkyl or $C_5$-$C_6$-cycloalkenyl, in which two substituents, together with the carbon atoms to which they are bonded, are $C_2$-$C_4$-alkanediyl or $C_2$-$C_4$-alkenediyl or butadienediyl, G is particularly preferably hydrogen (a) or one of the groups

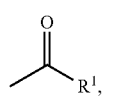
(b)

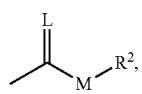
(c)

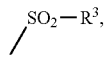
(d)

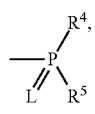
(e)

E, or (f)

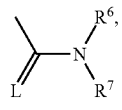
(g)

in which

E is a metal ion or an ammonium ion,

L is oxygen or sulphur and

M is oxygen or sulphur, $R^1$ is particularly preferably $C_1$-$C_{10}$-alkyl, $C_2$-$C_{10}$-alkenyl, $C_1$-$C_4$-alkoxy-$C_1$-$C_2$-alkyl, $C_1$-$C_4$-alkylthio-$C_1$-$C_2$-alkyl each of which is optionally mono- to trisubstituted by fluorine or chlorine, or is $C_3$-$C_6$-cycloalkyl optionally monosubstituted by fluorine, chlorine, methyl, ethyl or methoxy, is phenyl optionally mono- to disubstituted by fluorine, chlorine, bromine, cyano, nitro, methyl, ethyl, n-propyl, isopropyl, methoxy, ethoxy, trifluoromethyl or trifluoromethoxy, is furanyl, thienyl or pyridyl each of which is optionally monosubstituted by chlorine, bromine or methyl, $R^2$ is particularly preferably $C_1$-$C_{10}$-alkyl, $C_2$-$C_{10}$-alkenyl or $C_1$-$C_4$-alkoxy-$C_2$-$C_4$-alkyl each of which is optionally mono- to trisubstituted by fluorine or chlorine, is cyclopentyl or cyclohexyl or is phenyl or benzyl each of which is optionally mono- to disubstituted by fluorine, chlorine, cyano, nitro, methyl, ethyl, methoxy, trifluoromethyl or trifluoromethoxy, $R^3$ is particularly preferably methyl, ethyl, propyl or isopropyl each of which is optionally mono- to trisubstituted by fluorine or chlorine, or phenyl in each case optionally monosubstituted by fluorine, chlorine, bromine, methyl, ethyl, isopropyl, tert-butyl, methoxy, ethoxy, isopropoxy, trifluoromethyl, trifluoromethoxy, cyano or nitro, $R^4$ and $R^5$, independently of one another, are particularly preferably $C_1$-$C_4$-alkoxy or $C_1$-$C_4$-alkylthio or are phenyl, phenoxy or phenylthio each of which is optionally monosubstituted by fluorine, chlorine, bromine, nitro, cyano, methyl, methoxy, trifluoromethyl or trifluoromethoxy, $R^6$ and $R^7$, independently of one another, are particularly preferably hydrogen, $C_1$-$C_4$-alkyl, $C_3$-$C_6$-cycloalkyl, $C_1$-$C_4$-alkoxy, $C_3$-$C_4$-alkenyl or $C_1$-$C_4$-alkoxy-$C_2$-$C_4$-alkyl, phenyl optionally mono- to disubstituted by fluorine, chlorine, bromine, methyl, methoxy or trifluoromethyl, or together are a $C_5$-$C_6$-alkylene radical in which optionally one methylene group is replaced by oxygen or sulphur.

W is very particularly preferably hydrogen, chlorine, methyl, ethyl or methoxy, (emphasis on hydrogen, chlorine or methyl), X is very particularly preferably hydrogen, chlorine, methyl, ethyl, methoxy or ethoxy (emphasis on hydrogen, chlorine or methyl), Y and Z are very particularly preferably, independently of one another, hydrogen, chlorine, methyl or the radical

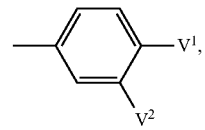

where in this case only one of the radicals Y or Z may be

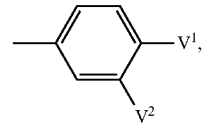

(most notably, Z is

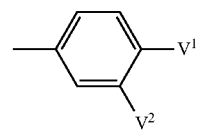

and Y is hydrogen)

$V^1$ is very particularly preferably hydrogen, fluorine or chlorine, (emphasis on hydrogen or chlorine), $V^2$ is very particularly preferably hydrogen, fluorine or chlorine (emphasis on hydrogen), A is very particularly preferably methyl, ethyl, propyl, isopropyl or cyclopropyl, (emphasis on methyl), B is very particularly preferably hydrogen or methyl, (emphasis on methyl), A, B and the carbon atom to which they are bonded are very particularly preferably saturated $C_5$-$C_6$-cycloalkyl in which optionally one ring member is replaced by oxygen and which is optionally monosubstituted by fluorine, chlorine, methyl, ethyl, methoxymethyl, methoxy, ethoxy, propoxy, butoxy, trifluoroethoxy, (emphasis on $C_6$-cycloalkyl which is substituted by methoxy), or A, B and the carbon atom to which they are bonded are very particularly preferably $C_6$-cycloalkyl which is optionally substituted by an alkylidenediyl group optionally interrupted by a with oxygen, or by an alkylidenediyl group containing with two non-directly adjacent oxygen atoms, where a 5- or 6-ring ketal is formed, each of which may be mono- or disubstituted by methyl, G is very particularly preferably hydrogen (a) or one of the groups

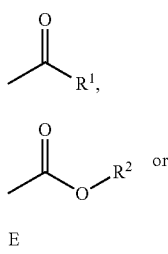

(b)

(c)

(f)

in which

E is a lithium, sodium, potassium, rubidium, caesium, magnesium, calcium ion or an ammonium ion, $R^1$ is very particularly preferably methyl, ethyl, propyl, isopropyl, butyl, isobutyl, sec-butyl, tert-butyl, cyclopropyl, cyclopentyl or cyclohexyl, $R^2$ is very particularly preferably methyl, ethyl, propyl, isopropyl, butyl, isobutyl, sec-butyl, tert-butyl, or is benzyl.

The radical definitions and explanations listed above in general terms or in preferred ranges can be combined as desired with one another, i.e. including between the respective ranges and preferred ranges. They apply accordingly for the end products and also for the pre-products and intermediates.

According to the invention, preference is given to the compounds of the formula (I) in which a combination of the meanings listed above as preferred (preferably) is present.

According to the invention, particular preference is given to the compounds of the formula (I) in which a combination of the meanings listed above as particularly preferred is present.

According to the invention, very particular preference is given to the compounds of the formula (I) in which a combination of the meanings listed above as very particularly preferred is present.

The compounds of the formula (II) required in the process (A*) as starting materials

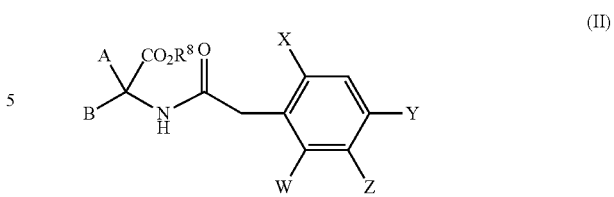

in which

A, B, W, X, Y, Z and $R^8$ have the meanings given above, are obtained, for example, when amino acid derivatives of the formula (VI)

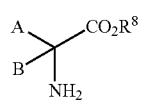

in which

A, B and $R^8$ have the meaning given above, are acylated with substituted phenylacetic acid derivatives of the formula (VII)

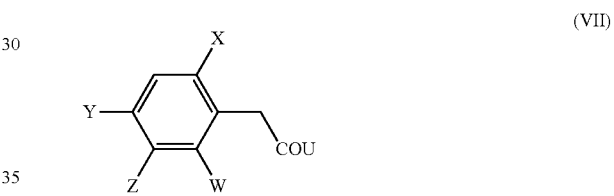

in which

W, X, Y and Z have the meanings given above and

U is a leaving group introduced via carboxylic acid activating reagents such as carbonyldiimidazole, carbonyldiimides (such as e.g. dicyclohexylcarbodiimide), phosphorylating reagents (such as e.g. $POCl_3$, BOP—Cl), halogenating agents such as e.g. thionyl chloride, oxalyl chloride or phosgene, and also via benzenesulphonyl chloride or chloroform is acid esters, (Chem. Reviews 52, 237-416 (1953); Bhattacharya, Indian J. Chem. 6, 341-5, 1968)

or when acylamino acids of the formula (VIII)

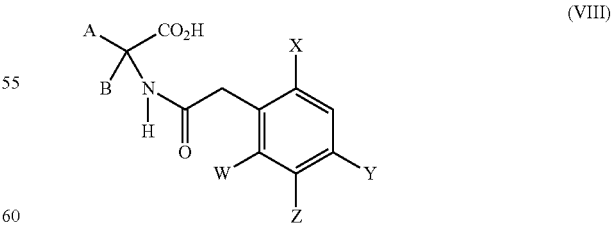

in which

A, B, W, X, Y and Z have the meanings given above, are esterified (Chem. Ind. (London) 1568 (1968)).

The compounds of the formula (VIII) are obtained for example when amino carboxylic acids of the formula (IX)

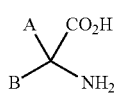

(IX)

in which
A and B have the meanings given above
are acylated with substituted phenylacetic acid derivatives of the formula (VII)

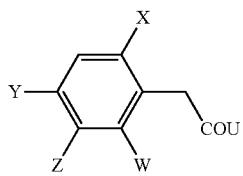

(VII)

in which
U, W, X, Y and Z have the meanings given above
e.g. according to Schotten-Baumann (Organikum [Organic Chemistry], V E B Deutscher Verlag der Wissenschaften, Berlin 1977, p. 505).

The compounds of the formulae (VI) and (IX) are known and can be synthesized by known processes (see e.g. Compagnon, Ann. Chim. (Paris) [14] 5, p. 11-22, 23-27 (1970), L. Munday, J. Chem. Soc. 4372 (1961); J. T. Eward, C. Jitrangeri, Can. J. Chem. 53, 3339 (1975), WO 02/02532), and also as described in the laid-open specifications cited at the start.

For these known processes, in each case substituted phenylacetic acid derivatives of the formula (VII)

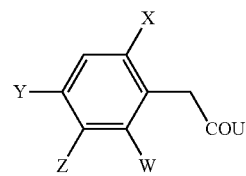

(VII)

in which U, W, X, Y and Z have the meanings given above, are thus required.

The compounds of the formula (VII) are known from the laid-open specifications cited at the start, such as e.g. WO 98/05638, WO 01/74770, and can be prepared by the processes described therein. Some of these processes are technically very complex, involve many stages or are encumbered with low total yields.

There was therefore furthermore a need for novel processes for the preparation of compounds of the general formula (I)

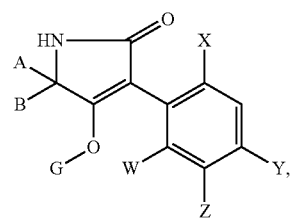

(I)

in which
A, B, W, X, Y, Z and G have the meanings given above, where X may additionally also be hydrogen, while avoiding the use of phenylacetic acid derivatives of the formula (VII).

It has already become known that for example 1,3-diketo compounds can be arylated with palladium catalysis (J. Amer. Chem. Soc. 2000, 122, 1360-70). Furthermore, it was known that Boc-protected tetramic acids can in principle be arylated starting from aryl chlorides, bromides and triflates, although the described method fails in the case of ortho substitutents (J. Org. Chem. 2009, 74, 5032-5040). Since in no example of the cited literature was a substrate with a functional NH group, as is present in tetramic acids of the formula (I), used, it was on the contrary to be assumed that such substrates may not be accessible to this reaction, especially not with ortho-substituted aryl radicals.

(Aα) Surprisingly, a process for the preparation of compounds of the formula (I) has now been found, characterized in that, in a first step, compounds of the formula (X)

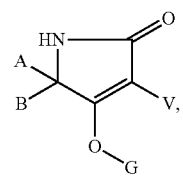

(X)

in which
A and B have the meanings given above,
G is the groups a), b), c) and E given above,
V is hydrogen or
(Aβ) V is COOR$^8$,
where R$^8$ is alkyl (preferably C$_1$-C$_8$-alkyl)
and A, B and G have the meanings given above,
are reacted with a compound of the formula (XI)

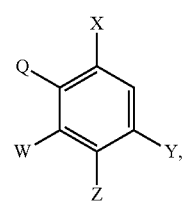

(XI)

in which
W, X, Y and Z have the meanings given above, with the exception that the halogen can now only be fluorine and chlorine, X may also additionally be hydrogen and
Q is triflate, bromine or iodine, preferably bromine or iodine,
in the presence of a base, a palladium catalyst and a phosphine ligand of the formula (XI')

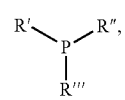

(XII')

in which the radicals
R', R" and R'" independently of one another are C$_1$-C$_{12}$-alkyl, C$_5$-C$_{10}$-cycloalkyl, C$_6$-C$_{10}$-aryl, which may be optionally mono- or polysubstituted by C$_1$-C$_6$-alkyl, C$_1$-C$_6$-alkoxy, C$_1$-C$_6$-alkylamino, C$_1$-C$_6$-dialkylamino, or are phenyl optionally mono- or polysubstituted by $C_1$-$C_6$-alkyl, $C_1$-$C_6$-alkoxy, $C_1$-$C_6$-alkylamino or $C_1$-$C_6$-dialkylamino, in a diluent.

The bases used for the process according to the invention are generally known organic and inorganic bases. Examples of organic bases are trimethylamine, triethylamine, tributylamine, diisopropylamine, diisopropylethylamine, N,N-dimethylaniline, DABCO, DBU, pyridine, picolines, luitidines, 5-ethyl-2-methylpyridine. Examples of inorganic bases are alkali metal and alkaline earth metal hydroxides such as LiOH, NaOH, KOH, Mg(OH)$_2$ and Ca(OH)$_2$, alkali metal alcoholates such as NaOMe, NaOEt, NaOtert-butyl, KOtert-butyl, alkali metal and alkaline earth metal carbonates such as Na$_2$CO$_3$, K$_2$CO$_3$, Cs$_2$CO$_3$ and CaCO$_3$ alkali metal and alkaline earth metal hydrogencarbonates such as NaHCO$_3$, KHCO$_3$, alkali metal and alkaline earth metal phosphates such as Na$_3$PO$_4$, K$_3$PO$_4$ and Mg$_3$(PO$_4$)$_2$, alkali metal and alkaline earth metal hydrogenphosphates such as Na$_2$HPO$_4$, K$_2$HPO$_4$ and BaHPO$_4$, alkali metal and alkaline earth metal dihydrogenphosphates such as NaH$_2$PO$_4$, KH$_2$PO$_4$ and Ca(H$_2$PO$_4$)$_2$, alkali metal and alkaline earth metal hydrides such NaH, KH and CaH$_2$ and alkali metal and alkaline earth metal amides such as NaNH$_2$, KNH$_2$ and LiNPr$_2$.

Preference is given to the alkali metal and alkaline earth metal carbonates and phosphates.

In the process according to the invention, the amount of base used can be varied within wide ranges. Usually, however, at least one molar equivalent of base, based on the compound of the general formula (X), will be used. It is also possible to use the base in excesses of from 1.1 to 15, preferably 1.1 to 6, mole equivalents of base based on the compound of the general formula (X).

Suitable palladium catalysts for the process according to the invention are in principle all palladium compounds from which an active catalyst can be formed in situ under the reaction conditions. Examples are: palladium chloride, palladium bromide, palladium iodide, palladium acetate, palladium trifluoroacetate, palladium nitrate, palladium sulphate, palladium acetyl-acetonate, allylpalladium chloride dimer, bis(dibenzylideneacetone)palladium, bis(triphenyl-phosphine)palladium(II) chloride, bis(triphenylphosphine)palladium(II) bromide, tetrakis(triphenylphosphine)palladium(0), bis(acetonitrile)palladium dichloride, bis(benzo-nitrile)palladium dichloride, 1,1'-bis(diphenylphosphino)ferrocene-palladium dichloride, di-μ-chlorobis(tri-tert-butylphosphino)dipalladium(I), di-μ-bromobis(tri-tert-butylphosphino)di-palladium(I), metallic palladium such as palladium black or palladium powder, or palladium on various supports such as, for example, palladium on activated carbon, palladium on barium sulphate, palladium on calcium carbonate or palladium on aluminium oxide.

The amount of palladium catalyst to be used in the process according to the invention can be varied within wide limits. Usually, the smallest possible amount with which a good yield is nevertheless achieved will be used. Typically, the amount of palladium catalyst is between 0.001 and 10 mol percent, based on the compound of the general formula (X). Preference is given to using amounts of from 0.01 to 5 mol percent.

Diluents which can be used for the process according to the invention are in principle all organic solvents that are inert under the reaction conditions. Examples are: ethers such as diethyl ether, methyl tert-butyl ether, methyl cyclopentyl ether, tetrahydrofuran, 2-methyltetrahydrofuran, 1,4-dioxane; hydrocarbons such as toluene, xylenes, mesitylene, chlorobenzene, 1,2-dichlorobenzene; amides such as N,N-dimethylformamide, N,N-dimethylacetamide, N-methylpyrrolidone; dimethyl sulphoxide or sulpholane.

In the process according to the invention, highly diverse phosphine ligands of the general formula (XI') can be used. Examples are: triphenylphosphine, tri-ortho-tolylphosphine, tri-meta-tolylphosphine, tri-para-tolylphosphine, benzyl-di-1-adamantylphosphine (cataCXium ABn), disodium bis(4,6-dimethyl-3-sulphonatophenyl)(2,4-dimethylphenyl)phosphine, trisodium tris(4,6-dimethyl-3-sulphonato-phenyl)phosphine, butyl di-1-adamantylphosphine (cataCXium A), tributylphosphine, tricyclohexylphosphine, tri-tert-butylphosphine, 2-di-tert-butylphosphino-1,1'-binaphthyl, 2-di-tert-butylphosphino-1,1'-biphenyl, 2-dicyclohexylphosphinobiphenyl, 2-di-tert-butylphosphino-2'-(N,N-dimethylamino)biphenyl, 2-dicyclohexylphosphino-2'-(N,N-dimethylamino)biphenyl, 2-di-tert-butylphosphino-2'-methylbiphenyl, 2-dicyclohexylphosphino-2'-methylbiphenyl, 2-dicyclohexylphosphino-2'-isopropylbiphenyl, 2-di-tert-butylphosphino-2',4',6'-triisopropyl-1,1'-biphenyl, 2-dicyclohexylphosphino-2',4',6'-triisopropyl-1,1'-biphenyl, 2-diphenylphosphino-2'-(N,N-dimethylamino)biphenyl, 2-dicyclohexylphosphino-2',6'-diisopropoxy-1,1'-biphenyl (RuPhos), N-(2-methoxyphenyl)-2-(di-tert-butylphosphino)pyrrole, N-phenyl-2-(di-tert-butyl-phosphino)pyrrole, 9,9-dimethyl-4,5-bis(diphenylphosphino)xanthene (XANTPHOS), 9,9-dimethyl-4,5-bis(di-tert-butylphosphino)xanthene, bis(2-diphenylphosphinophenyl)ether (DPEphos), 2,2'-bis(diphenylphosphino)-1,1'-biphenyl (BIPHEP), 2,2'-bis(diphenylphosphino)-1,1'-binaphthyl (BINAP), 1,1'-bis(diphenylphosphino)ferrocene (DPPF).

The amount of phosphine ligands of the general formula (XI') to be used in the process according to the invention is between 0.25 and 5 mol per mol of palladium catalyst. Preference is given to using between 0.5 and 2.5 mol per mol.

The reaction temperature for the process according to the invention can be varied within wide limits. Usually, the operating temperature is between 20 and 200° C., preferably between 50 and 180° C.

The process according to the invention is usually carried out at atmospheric pressure with the exclusion of atmospheric oxygen and moisture. However, the process can in principle also be carried out under reduced or increased pressure.

When carrying out the process according to the invention, it is possible to use the compounds of the formula (XI) in a relatively large excess (up to 10 mol, preferably up to 2 mol).

Some compounds of the formula (X) where G=hydrogen and substituted benzoyl are known in part from WO 94/01401, and also the literature stated therein, and some are novel.

The compounds of the formula (X)

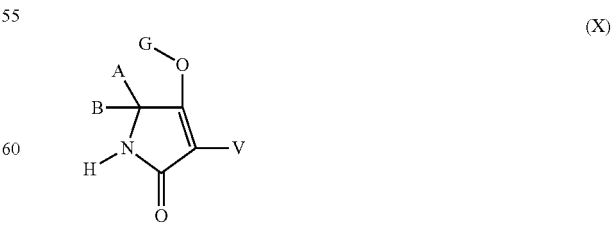

(X)

where

A, B and the carbon atom to which they are bonded are preferably saturated $C_5$-$C_6$-cycloalkyl, in which one ring member is replaced by oxygen or sulphur and which is optionally mono- or disubstituted by $C_1$-$C_6$-alkyl or $C_1$-$C_6$-alkoxy or A, B and the carbon atom to which they are bonded are preferably $C_3$-$C_6$-cycloalkyl, in which optionally one ring member is replaced by nitrogen and which is mono- or disubstituted, independently of one another, by $C_1$-$C_8$-alkyl, $C_1$-$C_8$-alkoxy, halogen, $C_3$-$C_8$-alkenyloxy, $C_1$-$C_6$-alkoxy-$C_1$-$C_6$-alkyl, $C_3$-$C_6$-cycloalkyl-$C_1$-$C_2$-alkoxy, $C_3$-$C_{10}$-cycloalkyl, $C_1$-$C_8$-haloalkyl, $C_2$-$C_6$-haloalkoxy or $C_1$-$C_6$-alkoxy-$C_1$-$C_4$-alkoxy, where the aforementioned radicals (with the exception of halogen and $C_1$-$C_8$-haloalkyl) are also suitable as N substituents and $C_1$-$C_8$-alkyl is only permitted in the event of a disubstitution, or A, B and the carbon atom to which they are bonded are preferably $C_5$-$C_6$-cycloalkyl which is substituted by an alkylenediyl group or by an alkylenedioxyl group or by an alkylenedithioyl group which optionally contains one or two non-directly adjacent oxygen and/or sulphur atoms and which is optionally substituted by $C_1$-$C_4$-alkyl, and which, with the carbon atom to which it is bonded, forms a further five- to eight-membered ring, G is preferably hydrogen (a) or one of the groups

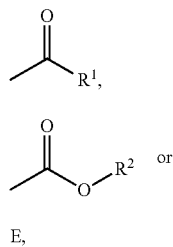

(b)

(c)

or (d)

E, in which

E is a metal ion or an ammonium ion, $R^1$ is preferably $C_1$-$C_8$-alkyl, $C_2$-$C_8$-alkenyl, $C_1$-$C_4$-alkoxy-$C_1$-$C_2$-alkyl, $C_1$-$C_4$-alkylthio-$C_1$-$C_2$-alkyl each of which is optionally mono- to trisubstituted by fluorine or chlorine, or $C_3$-$C_6$-cycloalkyl optionally mono- to disubstituted by fluorine, chlorine, $C_1$-$C_2$-alkyl or $C_1$-$C_2$-alkoxy, in which optionally one or two non-directly adjacent ring members are replaced by oxygen, is phenyl optionally mono- to disubstituted by fluorine, chlorine, bromine, cyano, nitro, $C_1$-$C_4$-alkyl, $C_1$-$C_4$-alkoxy, $C_1$-$C_2$-haloalkyl or $C_1$-$C_2$-haloalkoxy, $R^2$ is preferably $C_1$-$C_8$-alkyl, $C_2$-$C_8$-alkenyl or $C_1$-$C_4$-alkoxy-$C_2$-$C_4$-alkyl each of which is optionally mono- to trisubstituted by fluorine, is $C_3$-$C_6$-cycloalkyl optionally monosubstituted by $C_1$-$C_2$-alkyl or $C_1$-$C_2$-alkoxy, or is phenyl or benzyl each of which is optionally mono- to disubstituted by fluorine, chlorine, bromine, cyano, nitro, $C_1$-$C_4$-alkyl, $C_1$-$C_3$-alkoxy, trifluoromethyl or trifluoro-methoxy, V is preferably hydrogen (X-1) or $COOR^8$ (X-2), in which $R^8$ is preferably $C_1$-$C_8$-alkyl, are novel and likewise part of the invention.

Taking into consideration the various meanings (a), (b), (c) and (d) of group G, the following primary structures (X-1-a) to (X-1-d) arise when V is hydrogen,

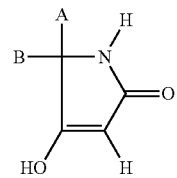

(X-1-a)

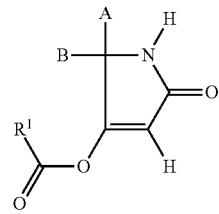

(X-1-b)

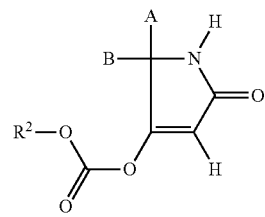

(X-1-c)

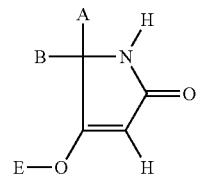

(X-1-d)

in which

A, B, E, $R^1$ and $R^2$ have the meanings given above.

Taking into consideration the various meanings (a), (b), (c) and (d) of group G, the following primary structures (X-2-a) to (X-2-d) arise when V is $COOR^8$,

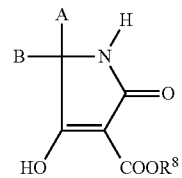

(X-2-a)

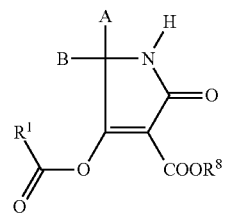

(X-2-b)

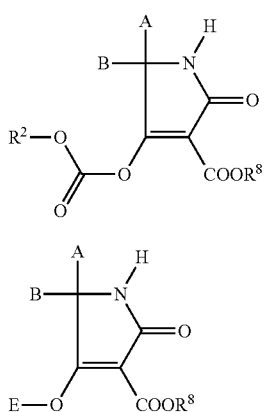

in which

A, B, E, $R^1$, $R^2$ and $R^8$ have the meanings given above.

The compounds according to the invention are generally defined by the formula (X). Preferred substituents and/or ranges of the radicals listed in the formulae mentioned above and below are explained hereinbelow:

A, B and the carbon atom to which they are bonded are particularly preferably saturated $C_5$-$C_6$-cycloalkyl, in which one ring member is replaced by oxygen or sulphur and which is optionally mono- to disubstituted by $C_1$-$C_4$-alkyl or $C_1$-$C_4$-alkoxy, or A, B and the carbon atom to which they are bonded are particularly preferably saturated $C_3$-$C_7$-cycloalkyl in which optionally one ring member is replaced by nitrogen and which is mono- to disubstituted, independently of one another, by $C_1$-$C_6$-alkyl, chlorine, fluorine, $C_1$-$C_4$-alkoxy-$C_1$-$C_2$-alkyl, trifluoromethyl, $C_1$-$C_6$-alkoxy, $C_3$-$C_6$-alkenyloxy, trifluoroethoxy, $C_1$-$C_3$-alkoxy-$C_1$-$C_3$-alkoxy or $C_3$-$C_6$-cycloalkylmethoxy, where the aforementioned radicals (with the exception of fluorine, chlorine and trifluoromethyl) are also suitable as N-substituents and $C_1$-$C_6$-alkyl is only permitted in the event of a disubstitution, or A, B and the carbon atom to which they are bonded are particularly preferably saturated $C_5$-$C_6$-cycloalkyl which is substituted by an alkylenediyl group or by an alkylenedioxyl group or by an alkylenedithiol group which optionally contains one or two non-directly adjacent oxygen or sulphur atoms and is optionally mono- or disubstituted by methyl or ethyl and which, with the carbon atom to which it is bonded, forms a further five- or six-membered ring, G is particularly preferably hydrogen (a) or one of the groups

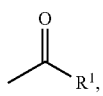

(b)

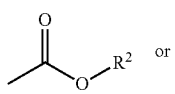

(c)

or (d)

E, in which

E is particularly preferably a metal ion or an ammonium ion, $R^1$ is particularly preferably $C_1$-$C_6$-alkyl, $C_2$-$C_6$-alkenyl, $C_1$-$C_2$-alkoxy-$C_1$-alkyl, $C_1$-$C_2$-alkylthio-$C_1$-alkyl each of which is optionally monosubstituted by chlorine, or cyclopropyl or cyclohexyl each of which is optionally monosubstituted by fluorine, chlorine, methyl or methoxy, is phenyl optionally monosubstituted by fluorine, chlorine, bromine, cyano, nitro, methyl, methoxy, trifluoromethyl or trifluoromethoxy, $R^2$ is particularly preferably $C_1$-$C_8$-alkyl, $C_2$-$C_6$-alkenyl or $C_1$-$C_4$-alkoxy-$C_2$-$C_3$-alkyl, phenyl or benzyl each of which is optionally monosubstituted by fluorine, V is particularly preferably hydrogen or $COOR^8$, in which $R^8$ is particularly preferably $C_1$-$C_6$-alkyl.

A, B and the carbon atom to which they are bonded are very particularly preferably saturated $C_5$-$C_6$-cycloalkyl in which one ring member is replaced by oxygen and which is optionally monosubstituted by methyl, ethyl, methoxy or ethoxy, or A, B and the carbon atom to which they are bonded are very particularly preferably saturated $C_5$-$C_6$-cycloalkyl in which optionally one ring member is replaced by nitrogen and which is mono- or disubstituted, independently of one another, by methyl, ethyl, trifluoromethyl, fluorine, methoxymethyl, ethoxymethyl, methoxyethyl, ethoxyethyl, methoxy, ethoxy, propoxy, butoxy, methoxyethoxy, ethoxyethoxy, allyloxy, trifluoroethoxy or cyclopropylmethoxy, where the aforementioned radicals (with the exception of fluorine and trifluoromethyl) are also suitable as N substituents and methyl or ethyl is only permitted in the event of a disubstitution, and or A, B and the carbon atom to which they are bonded are very particularly preferably $C_6$-cycloalkyl which is optionally substituted by an alkylidenediyl group optionally interrupted by an oxygen atom, or by an alkylenedioxy group containing with two non-directly adjacent oxygen atoms, where a 5- or 6-ring ketal is formed, each of which can optionally be mono- or disubstituted by methyl, G is very particularly preferably hydrogen (a) or one of the groups

(b)

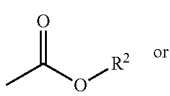

(c)

or (d)

E, in which

E is very particularly preferably a $Li^+$, $Na^+$, $K^+$ or $Cs^+$, $R^1$ is very particularly preferably methyl, ethyl, propyl, isopropyl, butyl, isobutyl, sec-butyl, tert-butyl, cyclopropyl or cyclohexyl, $R^2$ is very particularly preferably methyl, ethyl, propyl, isopropyl, butyl, isobutyl, sec-butyl, tert-butyl, phenyl or benzyl, V is very particularly preferably hydrogen or $COOR^8$, in which $R^8$ is very particularly preferably methyl, ethyl, propyl, isopropyl, butyl, isobutyl, sec-butyl, tert-butyl.

A, B and the carbon atom to which they are bonded are most notably saturated $C_6$-cycloalkyl in which one ring member is replaced by oxygen or A, B and the carbon atom to which they are bonded are most notably saturated $C_6$-cycloalkyl which is disubstituted by fluorine or monosubstituted by methoxy, or A, B and the carbon atom to which they are bonded are most notably $C_6$-cycloalkyl which is substituted by an alkylene-diyl group containing with two non-directly adjacent oxygen atoms, which, with the carbon atom to which it is bonded, forms a further five-membered ring, G is most notably hydrogen (a) or

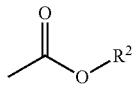
(c)

where $R^2$ is most notably ethyl,

V is most notably hydrogen (X-1) or $COOR^8$ (X-2), where $R^8$ is most notably methyl.

The radical definitions and explanations listed in general above or listed within preferred ranges can be combined as desired with one another, thus also between the respective ranges and preferred ranges. They apply accordingly for the end products and also for the pre-products and intermediates.

According to the invention, preference is given to the compounds of the formula (X) in which a combination of the meanings listed above as preferred (preferably) is present.

According to the invention, particular preference is given to the compounds of the formula (X) in which a combination of the meanings listed above as particularly preferred is present.

According to the invention, very particular preference is given to the compounds of the formula (X) in which a combination of the meanings listed above as very particularly preferred is present.

Emphasis is placed on compounds of the formula (X) in which G is hydrogen.

Saturated or unsaturated hydrocarbon radicals such as alkyl, alkanediyl or alkenyl can, including in combination with heteroatoms, such as e.g. in alkoxy, if possible, in each case be straight-chain or branched.

Unless stated otherwise, optionally substituted radicals can be mono- or polysubstituted, where in the case of polysubstitutions the substituents can be identical or different.

Specifically, apart from compounds specified in the examples, the following compounds of the formula (X) where G=H may be specified:

TABLE 1

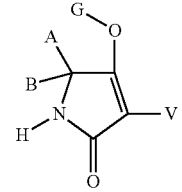
(X)

| A | B | V |
|---|---|---|
| —(CH$_2$)$_2$—O—(CH$_2$)$_2$— | | H |
| —CH$_2$—O—(CH$_2$)$_3$— | | H |
| —(CH$_2$)$_2$—S—(CH$_2$)$_2$— | | H |
| —CH$_2$—CHCH$_3$—(CH$_2$)$_3$— | | H |
| —CH$_2$—CHOCH$_3$—(CH$_2$)$_2$— | | H |
| —CH$_2$—CHOC$_2$H$_5$—(CH$_2$)$_2$— | | H |

TABLE 1-continued (X)

| A | B | V |
|---|---|---|
| —CH$_2$—CHOC$_3$H$_7$—(CH$_2$)$_2$— | | H |
| —CH$_2$—CHOC$_4$H$_9$—(CH$_2$)$_2$— | | H |
| —CH$_2$—CHO(CH$_2$)$_2$OCH$_3$—(CH$_2$)$_2$— | | H |
| —CH$_2$—CH(—O—cyclopropyl)—(CH$_2$)$_2$— | | H |
| —CH$_2$—CHOCH$_3$—(CH$_2$)$_3$— | | H |
| —CH$_2$—CHOC$_2$H$_5$—(CH$_2$)$_3$— | | H |
| —CH$_2$—CHOC$_3$H$_7$—(CH$_2$)$_3$— | | H |
| —CH$_2$—CHOC$_4$H$_9$—(CH$_2$)$_3$— | | H |
| —CH$_2$—CHO(CH$_2$)$_2$OCH$_3$—(CH$_2$)$_3$— | | H |
| —CH$_2$—CH(—O—cyclopropyl)—(CH$_2$)$_3$— | | H |
| —(CH$_2$)$_2$—CHOCH$_3$—(CH$_2$)$_2$— | | H |
| —(CH$_2$)$_2$—CHOC$_2$H$_5$—(CH$_2$)$_2$— | | H |
| —(CH$_2$)$_2$—CHOC$_3$H$_7$—(CH$_2$)$_2$— | | H |
| —(CH$_2$)$_2$—CHO—CH$_2$CF$_3$—(CH$_2$)$_2$— | | H |
| —(CH$_2$)$_2$—C(CH$_3$)$_2$—(CH$_2$)$_2$— | | H |
| —(CH$_2$)$_2$—(CHCH$_3$)$_2$—(CH$_2$)$_2$— | | H |
| —(CH$_2$)$_2$—CF$_2$—(CH$_2$)$_2$— | | H |
| —(CH$_2$)$_2$—C(spiro-tetrahydrofuran)—(CH$_2$)$_2$— | | H |
| —(CH$_2$)$_2$—C(spiro-1,3-dioxolane)—(CH$_2$)$_2$— | | H |
| —(CH$_2$)$_2$—C(spiro-4-methyl-1,3-dioxolane)—(CH$_2$)$_2$— | | H |
| —(CH$_2$)$_2$—C(spiro-4,5-dimethyl-1,3-dioxolane)—(CH$_2$)$_2$— | | H |
| —(CH$_2$)$_2$—C(spiro-1,3-dioxane)—(CH$_2$)$_2$— | | H |

TABLE 1-continued (X)

| A | B | V |
|---|---|---|
| —(CH₂)₂ | (CH₂)₂— with 2,2-dioxane-4-CH₃ | H |
| —(CH₂)₂ | (CH₂)₂— with 2,2-dioxane-5-CH₃ | H |
| —(CH₂)₂ | (CH₂)₂— with 2,2-dioxane-4,6-di-CH₃ | H |
| —(CH₂)₂ | (CH₂)₂— with 2,2-dioxane-5,5-di-CH₃ | H |
| —CH₂—CH(CH₂OCH₃)—(CH₂)₃— | | H |
| —CH₂—CH((CH₂)₂OCH₃)—(CH₂)₃— | | H |
| —(CH₂)₂—CH(CH₂OCH₃)—(CH₂)₂— | | H |
| —(CH₂)₂—CH((CH₂)₂OCH₃)—(CH₂)₂— | | H |
| —CH₂—CH(CH₂OCH₂CH₃)—(CH₂)₃— | | H |
| —CH₂—CH((CH₂)₂OCH₂CH₃)—(CH₂)₃— | | H |

TABLE 1-continued (X)

| A | B | V |
|---|---|---|
| —(CH₂)₂—CH(CH₂OCH₂CH₃)—(CH₂)₂— | | H |
| —(CH₂)₂—CH((CH₂)₂OCH₂CH₃)—(CH₂)₂— | | H |

Table 2 A and B as given in Table 1 and V=COOCH₃
Table 3 A and B as given in Table 1 and V=COOC₂H₅

(B) Compounds of the formula (X-2-a)

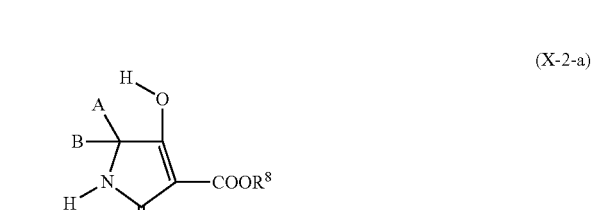

(X-2-a)

in which A, B and R⁸ have the meanings given above, are obtained when
compounds of the formula (XII)

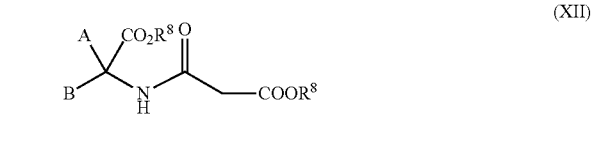

(XII)

in which
A, B and R⁸ have the meanings given above,
are intramolecularly condensed in the presence of a diluent and in the presence of a base.

(C) Moreover, compounds of the formula (X-1-a)

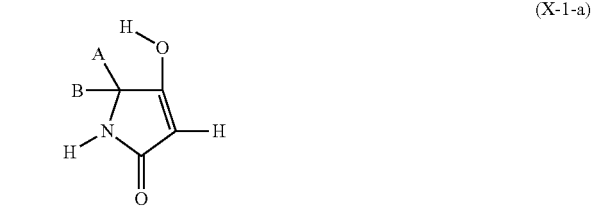

(X-1-a)

in which
A and B have the meanings given above, are obtained when
compounds of the formula (X-2-a)

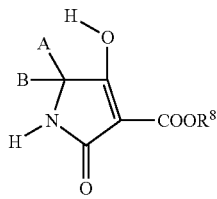
(X-2-a)

in which A, 13 and $R^8$ have the meanings given above,
are hydrolysed and then decarboxylated.

Furthermore, it has been found
(D) that the compounds of the formulae (X-1-b) or (X-2-b) shown above in which A, B and V have the meanings given above are obtained when compounds of the formulae (X-1-a) and (X-2-a) shown above in which A, B and V have the meanings given above, are reacted in each case
α) with compounds of the formula (III)

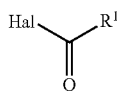
(III)

in which
$R^1$ has the meaning given above and
Hal is halogen (in particular chlorine or bromine)
or
β) with carboxylic anhydrides of the formula (IV)

$R^1$—CO—O—CO—$R^1$ (IV)

in which
$R^1$ has the meaning given above,
optionally in the presence of a diluent and optionally in the presence of an acid binder;
(E) that the compounds of the formulae (X-1-c) or (X-2-c) shown above in which $R^2$, A, B and in V have the meanings given above are obtained when compounds of the formulae (X-1-a) and sare reacted with chloroformic acid esters of the formula (V)

$R^2$—O—CO—Cl (V)

in which
$R^2$ has the meaning given above,
optionally in the presence of a diluent and optionally in the presence of an acid binder;
(F) that compounds of the formulae (X-1-d) and (X-2-d) shown above in which E, A, B and V have the meanings given above are obtained when compounds of the formulae (X-1-a) and (X-1-b) in which A, B and V have the meanings given above are in each case reacted
with metal compounds or amines of the formulae (XIII) or (XIV)

Me(OR$^{10}$)$_t$ (XIII)

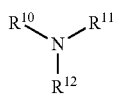
(XIV)

in which
Me is a mono- or divalent metal (preferably an alkali metal or alkaline earth metal such as lithium, sodium, potassium, caesium, magnesium or calcium),
t is the number 1 or 2 and
$R^{10}$, $R^{11}$, $R^{12}$, independently of one another, are hydrogen or alkyl (preferably $C_1$-$C_8$-alkyl), where in the case of Me $R^{10}$ may also be the group COO or HCOO
optionally in the presence of a diluent.

If, for example, according to process (Aα), 8-methoxy-1-azaspiro[4,5]decane-2,4-dione and 2,5-dimethylbromobenzene are used as starting materials, then the course of the reaction can be depicted by the following scheme:

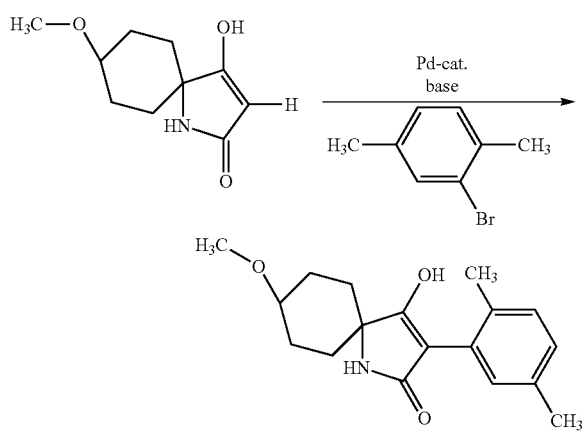

If, for example, according to process (Aβ), 3-methoxycarbonyl-8-methoxy-1-azaspiro-[4,5]-decane-2,4-dione and 2,5-dimethylbromobenzene are used as starting compounds, then the course of the process according to the invention can be depicted by the following reaction scheme:

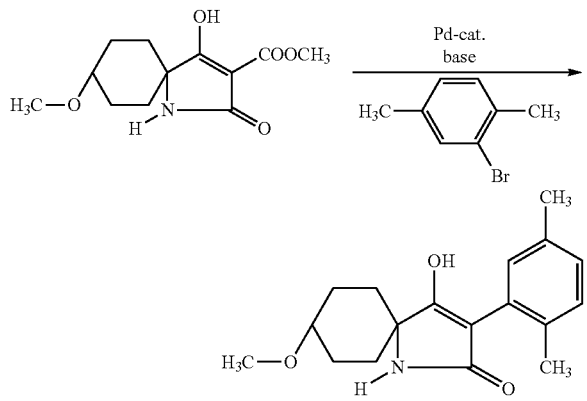

If, for example, according to process (B), N-ethoxycarbonylacetyl-1-amino-4-methoxy-cyclohexanecarboxylic acid ethyl ester is used as starting material, then the course of the process according to the invention can be depicted by the following reaction scheme:

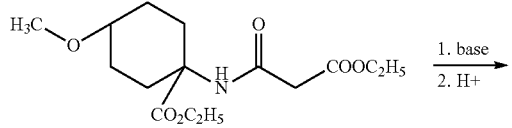

-continued

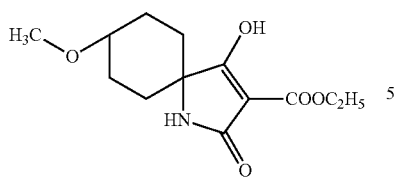

If, for example, according to process (C), 3-methoxycarbonyl-8-methoxy-1-azaspiro[4,5]decane-2,4-dione and an excess of aqueous base are used as starting materials, then the course of the reaction can be depicted by the following reaction scheme:

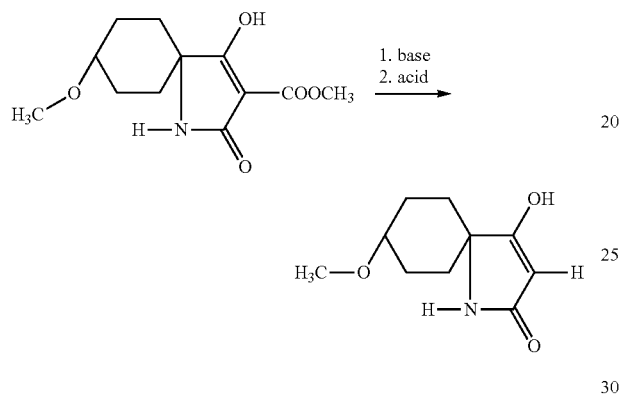

If, for example, according to process (Dα), 8-methoxy-1-azaspiro[4,5]decane-2,4-dione and acetyl chloride are used as starting materials, then the course of the process according to the invention can be depicted by the following reaction scheme:

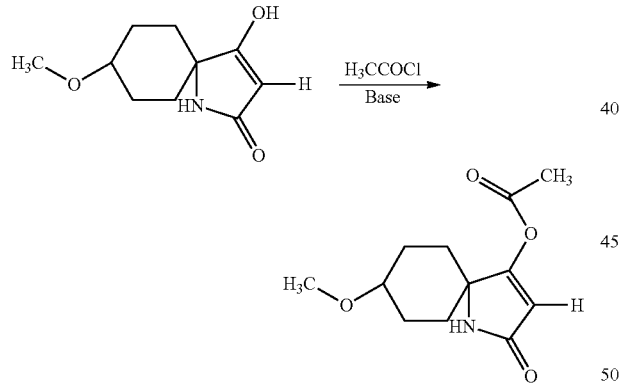

If, for example, according to process (Dβ), 8-methoxy-1-azaspiro-[4,5]-decane-2,4-dione and acetic anhydride are used as starting materials, then the course of the process according to the invention can be depicted by the following reaction scheme:

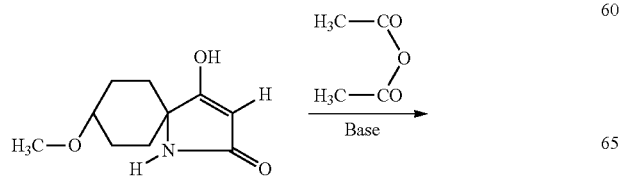

-continued

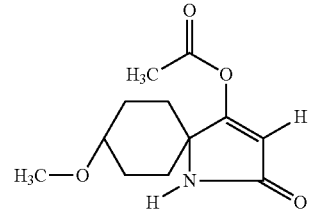

If, for example, according to process (E), 8-methoxy-1-azaspiro[4,5]decane-2,4-dione and chloroformic acid ethyl ester are used as starting compounds, then the course of the process according to the invention can be depicted by the following reaction scheme:

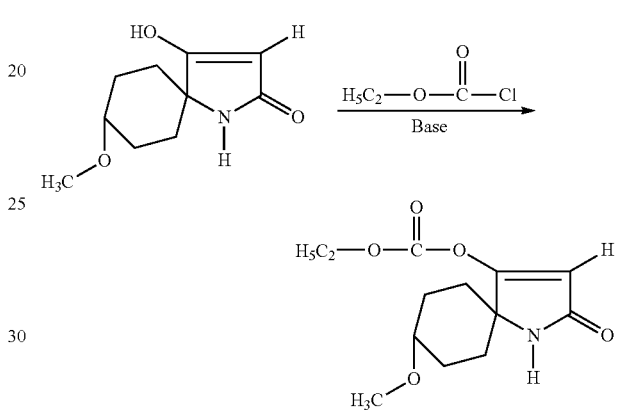

If, for example, according to process (F), 8-methoxy-1-azaspiro[4,5]decane-2,4-dione and for example sodium hydroxide (equimolar) are used as starting materials, then the course of the reaction can be depicted as follows:

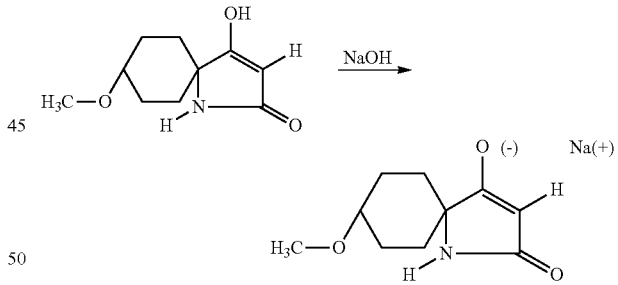

The compounds of the formula (XII) required as starting materials in the process (B) according to the invention

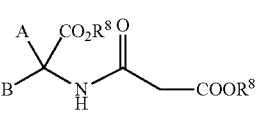

(XII)

in which
A, B and $R^8$ have the meanings given above,
are novel.
The acylamino acid esters of the formula (XII) are obtained for example when amino acid derivatives of the formula (XV)

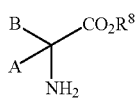

(XV)

in which
A, B and $R^8$ have the meaning given above,
are acylated with substituted malonic acid half-ester chlorides of the formula (XVI)

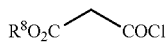

(XVI)

in which $R^8$ has the meanings given above,
(Chem. Reviews 52, 237-416 (19953); Bhattacharya, Indian J. Chem. 6, 341-5, 1968).

Furthermore, the starting materials of the formula (XII) used in the above process (B)

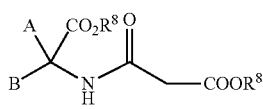

(XII)

in which
A, B and $R^8$ have the meanings given above,
can be prepared when 1-aminocarbonitriles of the formula (XVII)

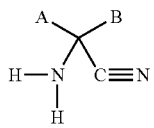

(XVII)

in which
A and B have the meanings given above,
are reacted with malonic acid half-ester chlorides of the formula (XVI)

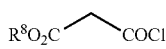

(XVI)

in which $R^8$ has the meanings given above,
to give compounds of the formula (XVIII)

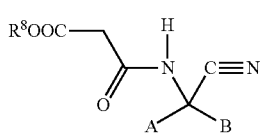

(XVIII)

in which
A, B and $R^8$ have the meanings given above,
and the latter are then subjected to an acidic alcoholysis.

The compounds of the formula (XVIII) are likewise novel and can be prepared analogously to known processes which are described in the literature cited at the start or e.g. as in EP-A-595 130. Some of the compounds of the formula (XVII) are commercially available, some are known, e.g. WO 2008/128058, and some are also novel and can be prepared e.g. as described in EP-A-595 130.

Moreover, the starting materials of the formula (XII) used in the above process (B)

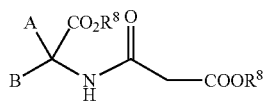

(XII)

in which
A, B and $R^8$ have the meanings given above,
can be prepared when 1-aminocarbonitriles of the formula (XVII)

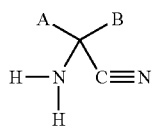

(XVII)

in which
A and B have the meanings given above,
are reacted with cyanoacetic acid of the formula (XIX)

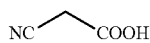

(XIX)

to give compounds of the formula (XX)

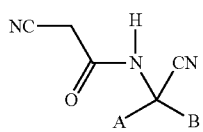

(XX)

in which
A and B have the meanings given above,
and the latter are then subjected to an acidic alcoholysis.

The compounds of the formula (XX) are likewise novel and can be prepared analogously by known processes which are described in the literature cited at the start.

The acid halides of the formula (III), carboxylic anhydrides of the formula (IV), chloroformic acid esters of the formula (V) and metal hydroxides, metal alkoxides, metal carbonates, metal hydrogencarbonates or amines of the formula (XIII) and (XIV) further required as starting materials for carrying out the processes (D), (E) and (F) according to the invention are generally known compounds in organic or inorganic chemistry.

Moreover, the compounds of the formulae (XV) and (XVII) are known from the patent applications cited at the start and/or can be prepared by the methods given therein.

The compounds of the formulae (XVI) and (XIX) are commercially available.

The process (B) is characterized in that compounds of the formula (XII) in which A, B and $R^8$ have the meanings given above are subjected to an intramolecular condensation in the presence of a diluent and in the presence of a base.

Diluents which can be used in the process (B) according to the invention are all organic solvents that are inert towards the reaction participants. The following can preferably be used: hydrocarbons, such as toluene and xylene, also ethers, such as dibutyl ether, tetrahydrofuran, dioxane, glycol dimethyl ether and diglycol dimethyl ether, also polar solvents, such as dimethyl sulphoxide, sulpholane, dimethylformamide and N-methylpyrrolidone, and also alcohols such as methanol, ethanol, propanol, isopropanol, butanol, isobutanol and tert-butanol.

All customary proton acceptors can be used as base (deprotonization agent) when carrying out the process (B) according to the invention. The following can preferably be used: alkali metal and alkaline earth metal oxides, hydroxides and carbonates, such as sodium hydroxide, potassium hydroxide, magnesium oxide, calcium oxide, sodium carbonate, potassium carbonate and calcium carbonate, which can also be used in the presence of phase transfer catalysts such as e.g. triethylbenzylammonium chloride, tetrabutylammonium bromide, Adogen 464 (=methyltrialkyl($C_8$-$C_{10}$)ammonium chloride) or TDA 1 (=tris(methoxyethoxyethyl)amine). Furthermore, alkali metals such as sodium or potassium can be used. It is also possible to use alkali metal and alkaline earth metal amides and hydrides, such as sodium amide, sodium hydride and calcium hydride, and moreover also alkali metal alcoholates, such as sodium methylate, sodium ethylate and potassium tert-butylate.

The reaction temperature can be varied within a relatively large range when carrying out the process (B) according to the invention. In general, working temperatures are between −75° C. and 200° C., preferably between −50° C. and 150° C. The process (A) according to the invention is generally carried out under atmospheric pressure.

When carrying out the process (B) according to the invention, the reaction component of the formula (XII) and the deprotonating base are generally used in equimolar amounts to about double-equimolar amounts. However, it is also possible to use the one or other component in a relatively large excess (up to 3 mol).

The process (C) is characterized in that compounds of the formula (X-2) in which A, B and $R^8$ have the meanings given above are hydrolysed and decarboxylated in the presence of a diluent and optionally in the presence of a base or acid.

Diluents which can be used in the process (C) according to the invention are all organic solvents which are inert towards the reaction participants. The following can preferably be used: ethers, such as tetrahydrofuran, dioxane, glycol dimethyl ether and diglycol dimethyl ether, moreover polar solvents, such as dimethyl sulphoxide, sulpholane, dimethyl formamide and N-methyl-pyrrolidone, and also alcohols such as methanol, ethanol, propanol, isopropanol, butanol, isobutanol and tert-butanol, but also water.

When carrying out the process (C) according to the invention, all customary lye-forming bases can be used as base. The following can preferably be used: alkali metal and alkaline earth metal oxides, hydroxides and carbonates, such as lithium hydroxide, sodium hydroxide, potassium hydroxide, magnesium oxide, calcium oxide, sodium carbonate, potassium carbonate and calcium carbonate.

When carrying out the process (C) according to the invention, all customary inorganic and organic acids can be used as acids. As inorganic acids, the following can preferably be used: e.g. hydrochloric acid, sulphuric acid, phosphoric acid and nitric acid. As organic acids, the following can preferably be used, e.g. formic acid, acetic acid, trifluoroacetic acid, oxalic acid, citric acid and aqueous solutions thereof.

As a special feature, the compounds of the formula (X-2) used in the process (C) can also be used autocatalytically as acid.

When carrying out the process (C) according to the invention, the reaction temperature can be varied within a relatively large range. In general, working temperatures are between −20° C. and 200° C., preferably between 0° C. and 150° C. The process (C) according to the invention is generally carried out under atmospheric pressure.

When carrying out the process (C) according to the invention, the reaction component of the formula (X-2) and the base or the acid are generally used in equimolar amounts up to about double-equimolar amounts. However, it is also possible to use the base or the acid in a relatively large excess, or else catalytically.

The process ($D_\alpha$) is characterized in that compounds of the formulae (X-1) or (X-2) are in each case reacted with carboxylic acid halides of the formula (III), optionally in the presence of a diluent and optionally in the presence of an acid binder.

Diluents which can be used in the process ($D_\alpha$) according to the invention are all solvents which are inert towards the acid halides. The following can preferably be used: hydrocarbons, such as benzine, benzene, toluene, xylene and tetralin, also halogenated hydrocarbons, such as methylene chloride, chloroform, tetrachloromethane, chlorobenzene and o-dichlorobenzene, moreover ketones, such as acetone and methyl isopropyl ketone, also ethers, such as diethyl ether, tetra-hydrofuran and dioxane, moreover carboxylic acid esters, such as ethyl acetate, and also strongly polar solvents, such as dimethylformamide, dimethyl sulphoxide and sulpholane. If the hydrolysis stability of the acid halide allows it, the reaction can also be carried out in the presence of water.

In the reaction according to the process ($D_\alpha$) according to the invention, suitable acid binders are all customary acid acceptors. The following can preferably be used: tertiary amines, such as triethylamine, pyridine, diazabicyclooctane (DABCO), diazabicycloundecene (DBU), diazabicyclononene (DBN), Hünig base and N,N-dimethylaniline, also alkaline earth metal oxides, such as magnesium oxide and calcium oxide, moreover alkali metal and alkaline earth metal carbonates, such as sodium carbonate, potassium carbonate and calcium carbonate, and also alkali metal hydroxides such as sodium hydroxide and potassium hydroxide.

The reaction temperature during the process ($D_\alpha$) according to the invention can be varied within a relatively large range. In general, working temperatures are between −20° C. and +150° C., preferably between 0° C. and 100° C.

When carrying out the process ($D_\alpha$) according to the invention, the starting materials of the formulae (X-1) or (X-2) and the carboxylic acid halide of the formula (III) are generally used in each case in approximately equivalent amounts. However, it is also possible to use the carboxylic acid halide in a relatively large excess (up to 5 mol). Work-up takes place in accordance with customary methods.

The process ($D_\beta$) is characterized in that compounds of the formulae (X-1) or (X-2) are reacted in each case with carboxylic anhydrides of the formula (IV) optionally in the presence of a diluent and optionally in the presence of an acid binder.

Diluents which can be used in the process ($D_\beta$) according to the invention are preferably those diluents which are also preferably contemplated in the case of the use of acid halides. Moreover, a carboxylic acid anhydride used in excess can also simultaneously act as diluent.

Suitable optionally added acid binders in the process ($D_\beta$) are preferably those acid binders which are also preferably contemplated in the case of the use of acid halides.

The reaction temperature during the process ($D_\beta$) according to the invention can be varied within a relatively large range. In general, working temperatures are between −20° C. and +150° C., preferably between 0° C. and 100° C.

When carrying out the process ($D_\beta$) according to the invention, the starting materials of the formulae (X-1) or (X-2) and the carboxylic acid anhydride of the formula (IV) are generally used in each case in approximately equivalent amounts. However, it is also possible to use the carboxylic acid anhydride in a relatively large excess (up to 5 mol). Work-up takes place in accordance with customary methods.

The procedure generally involves removing diluent and carboxylic acid anhydride, which is present in excess, and also the resulting carboxylic acid by distillation or by washing with an organic solvent or with water.

The process (E) is characterized in that compounds of the formulae (X-1) or (X-2) are in each case reacted with chloroformic acid esters of the formula (V), optionally in the presence of a diluent and optionally in the presence of an acid binder.

Suitable acid binders in the process (E) according to the invention are all customary acid acceptors. The following can preferably be used: tertiary amines, such as triethylamine, pyridine, DABCO, DBU, DBN, Hünig base and N,N-dimethylaniline, also alkaline earth metal oxides, such as magnesium oxide and calcium oxide, furthermore alkali metal and alkaline earth metal carbonates, such as sodium carbonate, potassium carbonate and calcium carbonate, and also alkali metal hydroxides such as sodium hydroxide and potassium hydroxide.

Diluents which can be used in the process (E) according to the invention are all solvents that are inert towards the chloroformic acid esters. The following can preferably be used: hydrocarbons, such as benzine, benzene, toluene, xylene and tetralin, also halogenated hydrocarbons, such as methylene chloride, chloroform, tetrachloromethane, chlorobenzene and o-dichlorobenzene, furthermore ketones, such as acetone and methyl isopropyl ketone, also ethers, such as diethyl ether, tetrahydrofuran and dioxane, moreover carboxylic acid esters, such as ethyl acetate, moreover nitriles such as acetonitrile and also strongly polar solvents, such as dimethylformamide, dimethylsulphoxide and sulpholane.

When carrying out the process (E) according to the invention, the reaction temperature can be varied within a relatively large range. The reaction temperature is generally between −20° C. and +100° C., preferably between 0° C. and 50° C.

The process (E) according to the invention is generally carried out under atmospheric pressure.

When carrying out the process (E) according to the invention, the starting materials of the formulae (X-1) or (X-2) and the corresponding chloroformic acid ester of the formula (V) are generally used in each case in approximately equivalent amounts. However, it is also possible to use the one or other component in a relatively large excess (up to 2 mol). Work-up takes place by customary methods. In general, the procedure involves removing precipitated salts and concentrating the remaining reaction mixture by drawing off the diluent.

The process (F) is characterized in that compounds of the formulae (X-1) or (X-2) are in each case reacted with metal amides, metal hydrides, metal hydroxides, metal alkoxides, metal carbonates or metal hydrogencarbonates of the formula (XIII) or amines of the formula (XIV), which are specified in the case of the process (A) according to the invention, optionally in the presence of a diluent.

Diluents which can be used in the process (F) according to the invention are preferably the solvents specified in the case of process (A), but also alcohols such as methanol, ethanol, iso-propanol, and also water. The process (F) according to the invention is generally carried out under atmospheric pressure. The reaction temperature is generally between −20° C. and 100° C., preferably between 0° C. and 50° C.

PREPARATION EXAMPLES

Note: Me stands for methyl; Et stands for ethyl

Example 1

5,5-Dimethyl-3-phenylpyrrolidine-2,4-dione

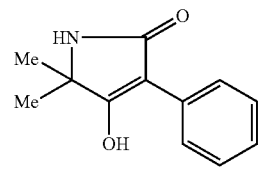 [SMILES: CC1(C)NC(=O)C(c2ccccc2)=C1O]

Under argon, in a heat-dried apparatus, 23 mg of Pd(OAc)$_2$, 69 mg of di-tert-butyl(2'-methylbiphenyl-2-yl)phosphine and 2.44 g of K$_3$PO$_4$ in 15 ml of air-free dioxane are introduced as initial charge. 763 mg of 5,5-dimethylpyrrolidine-2,4-dione and 785 mg of bromobenzene are added and the mixture is stirred for 16 hours under reflux. The mixture is then left to cool to room temperature, diluted with 20 ml of methanol and filtered, and the filter residue is afterwashed with 10 ml of MeOH. The combined filtrates are concentrated by evaporation on a rotary evaporator. The residue is taken up in 20 ml of water and rendered weakly acidic using dilate hydrochloric acid. The precipitated solid is filtered off with suction and washed with 10 ml of water. It is then washed from the filter with acetone and the filtrate is concentrated by evaporation. This gives 1.01 g of solid with a purity of 93.8% according to GC/MS.

GC/MS: m/e=203 (M$^+$, 20%), 118 (M-NHCMe$_2$CO; 100%).

$^1$H-NMR (400 MHz, d-DMSO): δ=1.35 (s, 6H), 7.13-7.17 (m, 1H), 7.28-7.32 (m, 2H), 7.65 (s, 1H), 7.91-7.93 (m, 2H), 11.08 (s, 1H) ppm.

Example 2

5,5-Dimethyl-3-(2-methylphenyl)pyrrolidine-2,4-dione

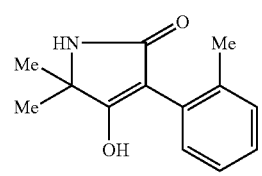 [SMILES: Cc1ccccc1C1=C(O)C(C)(C)NC1=O]

The procedure is as in Example 1, except that 855 mg of 2-bromotoluene are used instead of bromobenzene. This gives 0.84 g of solid with a purity according to GC/MS of 86.3%.

GC/MS: m/e=217 (M$^+$, 30%), 132 (M-NHCMe$_2$CO, 100%).

Example 3

5,5-Dimethyl-3-(3-methylphenyl)pyrrolidine-2,4-dione

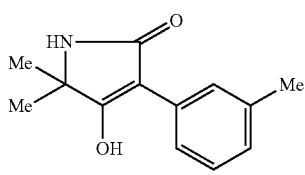 [SMILES: Cc1cccc(C2=C(O)C(C)(C)NC2=O)c1]

The procedure is as in Example 1, except that 855 mg of 3-bromotoluene are used instead of bromobenzene. This gives 1.17 g of solid with a purity according to GC/MS of 92%.

GC/MS: m/e=217 (M$^+$, 20%), 132 (M-NHCMe$_2$CO, 100%).

Example 4

5,5-Dimethyl-3-(3-methylphenyl)pyrrolidine-2,4-dione

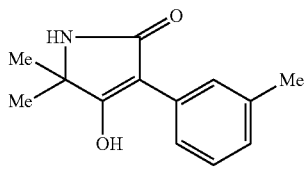 [SMILES: Cc1cccc(C2=C(O)C(C)(C)NC2=O)c1]

Under argon, in a heat-dried apparatus, 1.0 g of solid sodium hydroxide (in the form of so-called "Micropills") and 15 ml of water- and air-free N-methylpyrrolidone (NMP) are introduced as initial charge. With stirring, 1.907 g of 5,5-dimethylpyrrolidine-2,4-dione are then added and the mixture is stirred for 20 minutes at room temperature. 1.71 g of 3-bromotoluene are then added and the reaction mixture is heated to 125° C. At this temperature, 0.328 g of triphenylphosphine and 89 mg of PdCl$_2$ are then added. The mixture is stirred for 4 hours at 125° C., left to cool to room temperature, stirred into 20 ml of ice-water and adjusted to pH 2 using dilute hydrochloric acid. 20 ml of methylene chloride are added, the mixture is stirred, the phases are separated and the aqueous phase is extracted by shaking two more times with 10 ml of methylene chloride in each case. The combined organic phases are dried and then concentrated on a rotary evaporator. This gives 1.82 g of target product (corresponding to a yield of 84% of theory).

Example 5

3-(4-Chloro-2-methylphenyl)-5,5-dimethylpyrrolidine-2,4-dione

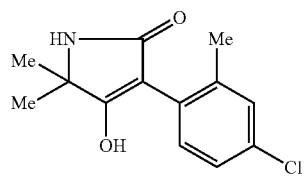 [SMILES: Cc1cc(Cl)ccc1C1=C(O)C(C)(C)NC1=O]

The procedure is as in Example 1, except that 1.03 g of 2-bromo-5-chlorotoluene are used instead of bromobenzene. This gives 1.37 g of solid with a purity according to GC/MS of 94.3%.

GC/MS: m/e=251 (M$^+$ for $^{35}$Cl, 25%), 166 (M-NHCMe$_2$CO, 100%).

Example 6

3-(Biphenyl-3-yl)-5,5-dimethylpyrrolidine-2,4-dione

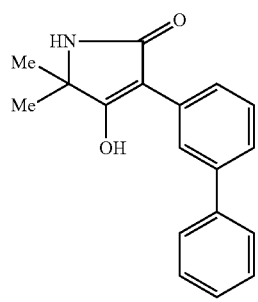 [SMILES: CC1(C)NC(=O)C(c2cccc(-c3ccccc3)c2)=C1O]

The procedure is as in Example 1, except that 1.166 g of 3-bromobiphenyl are used instead of bromobenzene. This gives 1.52 g of solid with a purity according to GC/MS of 95.4%.

GC/MS: m/e=279 (M$^+$, 35%), 194 (M-NHCMe$_2$CO, 90%), 165 (100%).

Example 7

3-(2,5-Dimethylphenyl)-5,5-dimethylpyrrolidine-2,4-dione

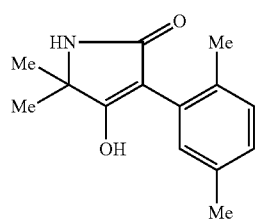 [SMILES: Cc1ccc(C)c(C2=C(O)C(C)(C)NC2=O)c1]

The procedure is as in Example 1, except that 0.926 g of 2,5-dimethylbromobenzene are used instead of bromobenzene. This gives 1.21 g of solid with a purity according to GC/MS of 90%.

GC/MS: m/e=231 (M+, 20%), 146 (M-NHCMe₂CO, 100%).

Example 8

8-Methoxy-3-phenyl-1-azaspiro[4.5]decane-2,4-dione

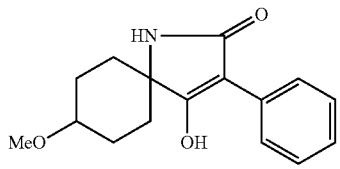 [SMILES: COC1CCC2(CC1)NC(=O)C(c1ccccc1)=C2O]

The procedure is as in Example 1, except that 1.18 g of 8-methoxy-1-azaspiro[4.5]decane-2,4-dione are used instead of 5,5-dimethylpyrrolidine-2,4-dione. This gives approximately 336 mg of the title compound.
GC/MS: m/e=273 (M+, 15%), 241 (M-MeOH, 5%), 118 (PhCHCO; 100%).

Example 9

2,2-Dimethyl-5-oxo-4-phenyl-2,5-dihydro-1H-pyrrol-3-yl ethylcarbonate

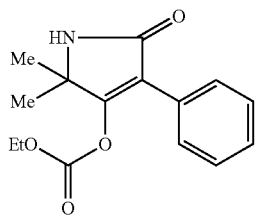 [SMILES: CCOC(=O)OC1=C(c2ccccc2)C(=O)NC1(C)C]

The procedure is as in Example 1, except that 1.195 g of 2,2-dimethyl-5-oxo-2,5-dihydro-1H-pyrrol-3-yl ethylcarbonate are used instead of 5,5-dimethylpyrrolidine-2,4-dione. This gives the title compound in a yield of 69% of theory.
GC/MS: m/e=275 (M+, 2%), 203 (M-72, 80%), 188 (100%), 145 (95%), 118 (M-EtOCO, —NHCMe₂CO, 70%), 89 (100%).

Example 10

2,2-Dimethyl-5-oxo-4-phenyl-2,5-dihydro-1H-pyrrol-3-yl acetate

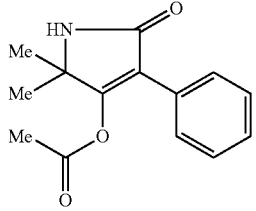 [SMILES: CC(=O)OC1=C(c2ccccc2)C(=O)NC1(C)C]

The procedure is as in Example 1, except that 1.015 g of 2,2-dimethyl-5-oxo-2,5-dihydro-1H-pyrrol-3-yl acetate are used instead of 5,5-dimethylpyrrolidine-2,4-dione. This gives the title compound in a yield of about 35% of theory. Additionally, as a result of in situ elimination of the acetyl radical, 5,5-dimethyl-3-phenylpyrrolidine-2,4-dione is obtained in a yield of approximately 38% of theory.
GC/MS: m/e=245 (M+, 2%), 203 (M-42, 100%), 188 (60%), 118 (80%), 43 (50%).

Example 11

8-Methoxy-3-phenyl-1-azaspiro[4.5]decane-2,4-dione

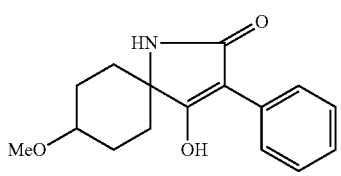 [SMILES: COC1CCC2(CC1)NC(=O)C(c1ccccc1)=C2O]

The procedure is as in Example 1, except that 1.532 g of methyl 8-methoxy-2,4-dioxo-1-azaspiro[4.5]decane-3-carboxylate as in Example (X-2-a-1) are used instead of 5,5-dimethyl-pyrrolidine-2,4-dione. This gives the title compound in a yield of approximately 90% of theory.

Example 12

3-(4-Chloro-2-methylphenyl)-8-methoxy-1-azaspiro[4.5]decane-2,4-dione

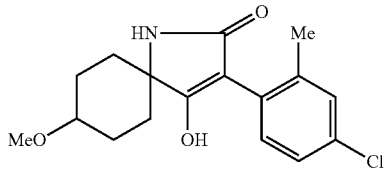 [SMILES: COC1CCC2(CC1)NC(=O)C(c1ccc(Cl)cc1C)=C2O]

The procedure is as in Example 11, except that 1.03 g of 2-bromo-5-chlorotoluene are used instead of bromobenzene. This gives the title compound in a yield of approximately 22% of theory.
GC/MS: m/e=321 (M+ for ³⁵Cl, 20%), 290 (M-31, 20%), 166 (100%).

Example 13

3-(2,5-Dimethylphenyl)-8-methoxy-1-azaspiro[4.5]decane-2,4-dione

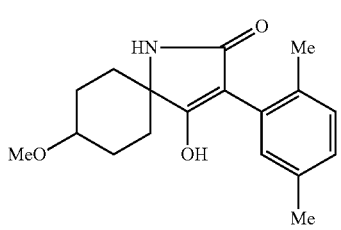 [SMILES: COC1CCC2(CC1)NC(=O)C(c1cc(C)ccc1C)=C2O]

The procedure is as in Example 11, except that 0.925 g of 2,5-dimethylbromobenzene are used instead of bromobenzene. This gives the title compound in a yield of approximately 20% of theory.

GC/MS: m/e=301 (M+20%), 270 (M-31, 20%), 146 (100%).

Example 14

3-[3-(4-chlorophenyl)-6-methylphenyl]-5,5-dimethylpyrrolidine-2,4-dione

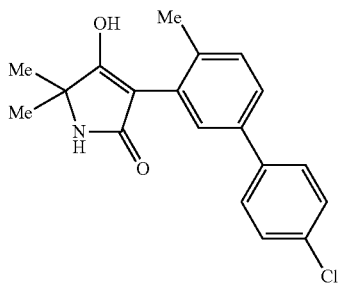 [SMILES: Cc1ccc(-c2ccc(Cl)cc2)cc1C1=C(O)C(C)(C)NC1=O]

Under argon, in a heat-dried apparatus, 7.4 mg of $Pd(OAc)_2$, 22 mg of di-tert-butyl(2'-methylbiphenyl-2-yl)phosphine and 0.78 g of $K_3PO_4$ in 4.8 ml of air-free dioxane are introduced as initial charge. 203 mg of 5,5-dimethylpyrrolidine-2,4-dione and 659 mg of 3-(4-chlorophenyl)-6-methylbromobenzene are added and the mixture is stirred for 16 hours under reflux. The mixture is then left to cool to room temperature, diluted with ca. 6 ml of methanol and filtered, and the filter residue is after-washed with ca. 3 ml of MeOH. The combined filtrates are concentrated by evaporation on a rotary evaporator. The residue is taken up in ca. 6 ml of water and rendered weakly acidic using 1 N hydrochloric acid. The precipitated solid is filtered off with suction and washed with ca. 3 ml of water. It is then washed from the filter with acetone and the filtrate is concentrated by evaporation. This gives 0.597 g of solid. Reversed-phase separation with water/acetonitrile (gradient) gives 93 mg (14% of theory) with a purity of 98.6% according to HPLC/MS.

$^1$H-NMR (400 MHz, $d_6$-DMSO): δ=1.36 (s, 6H, 2×$CH_3$), 2.20 (s, 3H, Ar—$CH_3$), 7.29-7.31 (d, 1H, ArH), 7.35 (d, 1H, ArH), 7.47-7.51 (m, 3H, ArH), 7.61 (br, 1H, NH), 7.63-7.67 (m, 2H, ArH), 10.83 (s, br, 1H, OH) ppm.

Example (X-1-a-1)

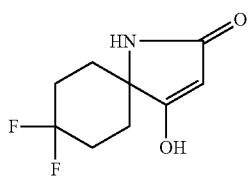

500 mg (1.9 mmol) of the compound according to Ex. X-2-a-4 are introduced in portions into a boiling 50% strength ethanol/water mixture over the course of 5 minutes. The mixture is stirred under reflux until the evolution of $CO_2$ has finished, the mixture is concentrated on a rotary evaporator, and the residue is recrystallized from ethanol. This gives 275 mg of a colourless powder (69% of theory).

$^1$H-NMR (400 MHz, $CDCl_3$): δ=1.79-1.84 (m, 2H), 1.94-2.11 (2m, 4H), 2.20-2.33 (m, 2H), 3.13 (s, 2H, CO—$CH_2$—CO), 7.52 (br, 1H, NH) ppm.

$^1$H-NMR (400 MHz, $CD_3CN$): δ=1.78-1.82 (m, 2H), 1.90-2.06 (2m, 4H), 2.12-2.18 (m, 2H), 3.03 (s, 2H, CO—$CH_2$—CO), 7.27 (br, 1H, NH) ppm.

Example (X-2-a-1)

Process B

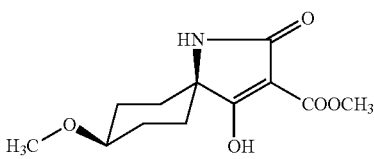

28.7 g (0.1 mol) of the compound according to Ex. XII-1 are introduced into 100 ml of absolute methanol. At 20° C., 19.5 ml of sodium methylate solution (30% strength in methanol) are added dropwise and the mixture is then stirred for 4 h at 40° C. The solvent is evaporated off in vacuo, the residue is taken up with 50 ml of water, and, at 0° C., 110 ml of 1 N hydrochloric acid are added dropwise. Upon evaporation in vacuo, the product precipitates out, is then suspended in 50 ml of ice-water and filtered off with suction.

Yield: 25 g (97% of theory) m.p. decomposition.

$^1$H-NMR (400 MHz, $d_6$-DMSO): δ=1.32-1.35 ("d", 2H), 1.39-1.49 (m, 2H), 1.65-1.73 (tm, 2H), 1.90-194 (dm, 2H), 3.09-3.16 (zm, 1H, $CHOCH_3$.cis), 3.24 (s, 3H, $OCH_3$), 3.59 (s, 3H, $COOCH_3$) ppm.

HPLC retention time 0.97 (method: column 50×4.6 mm Eclipse Plus $C_{18}$; 1.8 μm, gradient 0.1% phosphoric acid/acetonitrile; flow: 2 ml/min, 55° C.)

The following compounds of the formula (X-2-a) are obtained analogously to Example (X-2-a-1) and according to the general preparation instructions:

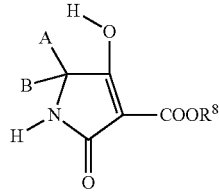

(X-2-a)

| Ex. No. | A | B | R⁸ | m.p. °C.; analytics * |
|---|---|---|---|---|
| X-2-a-2 | —$(CH_2)_2$—O—$(CH_2)_2$— | | $CH_3$ | 324; *¹ |
| X-2-a-3 | —$(CH_2)_2$—C(OCH₂CH₂O)—$(CH_2)_2$— | | $CH_3$ | *² |
| X-2-a-4 | —$(CH_2)_2$—$CF_2$—$(CH_2)_2$— | | $CH_3$ | *³ |

*¹ $^1$H-NMR (400 MHz, $CD_3OD$): δ = 1.43-1.47 (dd, 2H), 2.05-2.13 (tm, 2H), 3.66-3.72 (td, 2H, $OCH_2$), 3.80 (s, 3H, $COOCH_3$), 3.96-4.00 (d, m, 2H, $OCH_2$) ppm.
*² $^1$H-NMR (400 MHz, $d_6$-DMSO): δ = 1.17-1.2 (d, 2H), 1.56-1.86 (m, 6H), 3.46 (s, 3H, $CO_2CH_3$), 3.84 (s, 4H, —O($CH_2$)₂—O), 7.23 (br, 1H, NH) ppm.
*³ $^1$H-NMR (600 MHz, $d_6$-DMSO): δ = 1.52-1.54 (d, br, 2H), 1.91 (cm, br, 2H), 2.11-2.13 (2"d, br", 4H), 3.66 (s, 3H, $CO_2CH_3$), 8.85 (br, 1H, NH) ppm.

Example XII-1

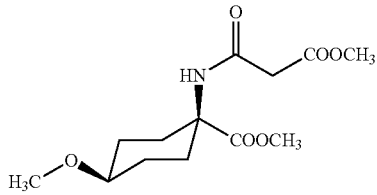

117.4 g (0.525 mol) of cis-1-amino-4-methoxycyclohexanecarboxylic acid methyl ester hydrochloride are introduced into 1000 ml of absolute tetrahydrofuran (THF), admixed with 153.3 ml (1.1 mol) of triethylamine and, at 20° C., 68.3 g (0.5 mol) of malonic acid methyl ester chloride in 30 ml of absolute THF are added dropwise. The mixture is then stirred for 4 h at 40° C., poured onto 1 l of water and extracted with methylene chloride, and the organic phase is dried and evaporated in vacuo.

The residue (172 g) is purified by column chromatography over silica gel with methylene chloride/ethyl acetate 2:1 as eluent.

Yield: 85.6 g (59.6% of theory), m.p. 74° C.

$^1$H-NMR (400 MHz, $CD_3CN$): δ=1.34-1.44 (qm, 2H), 1.73-1.81 (tm, 2H), 1.85-195 (m, 2H), 2.06-2.12 (dm, 2H), 3.15-3.22 (zm, 1H, C$\underline{H}$OCH$_3$-cis), 3.24 (s, 2H, C$\underline{H_2}$COOCH$_3$), 3.28 (s, 3H, OCH$_3$), 3.60, 3.68 (2s, in each case 3 H, COOC$\underline{H_3}$), 6.88 (s, br, 1 H, NH) ppm.

The following compounds of the formula (XII) are obtained analogously to Example (XII-1) and according to the general preparation instructions:

(XII)

A-C(CO$_2$R$^8$)(B)-NH-CO-COOR$^8$

| Ex. No. | A | B | R$^8$ | m.p. ° C.; analytics * |
|---|---|---|---|---|
| XII-2 | —(CH$_2$)$_2$—O—(CH$_2$)$_2$— | | CH$_3$ | 62; *1 |
| XII-3 | —(CH$_2$)$_2$—C(O—CH$_2$—CH$_2$—O)—(CH$_2$)$_2$— | | CH$_3$ | *2 |
| XII-4 | —(CH$_2$)$_2$—CF$_2$—(CH$_2$)$_2$— | | CH$_3$ | *3 |

*1 $^1$H-NMR (400 MHz, CD$_3$CN): δ = 1.41-1.46 (dm, 1H), 1.86-2.08 (m, 3H), 3.25 (s, 2H, COCH$_2$CO), 3.52-3.80 (m, 4H, OCH$_2$), 3.64, 3.68 (2s, in each case 3H, COOMe), 7.06 (sbr, 1H, NH) ppm.

*2 $^1$H-NMR (400 MHz, CDCl$_3$): δ = 1.67-1.76 (m, 4H), 2.14-2.19 (m, 4H), 3.34 (s, 2H, CO—CH$_2$—CO), 3.72, 3.77 (2s, in each case 3H, CO$_2$CH$_3$,), 3.96 (s, 4H, —O—(CH$_2$)$_2$—O), 7.67 (s, br, 1H, NH) ppm.

*3 $^1$H-NMR (400 MHz, d$_6$-DMSO): δ = 1.86-2.14 (m, 8H), 3.58 (s, 2H, COCH$_2$CO$_2$CH$_3$), 3.60, 3.63 (2s, in each case 3H, CO$_2$CH$_3$), 8.57 (s, br, 1H, NH) ppm.

Example X-1-b-1

2,2-Dimethyl-5-oxo-2,5-dihydro-1H-pyrrol-3-yl acetate

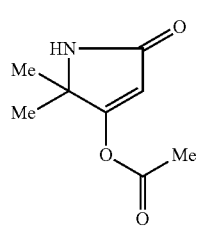

(X-1-b-1)

At 0 to 5° C., a solution of 4.08 g of acetyl chloride in 20 of methylene chloride is added dropwise to a solution of 6.36 g of 5,5-dimethylpyrrolidine-2,4-dione and 5.57 g of triethylamine in 50 ml of methylene chloride. The mixture is then left to reach room temperature over the course of approximately one hour and then stirred for a further 24 hours. The reaction mixture is then diluted with 50 ml of methylene chloride, and extracted by shaking twice with in each case 50 ml of water, twice with in each case 25 ml of 5% strength sodium hydroxide solution and once with 50 ml of saturated aqueous NaCl solution. Drying and concentration by evaporation gives 1.58 g of the title compound in a purity according to HPLC of 97%.

LC/MS: m/e=170 (MH$^+$).

$^1$H-NMR (400 MHz, CDCl$_3$): δ=1.33 (s, 6H), 2.23 (s, 3H), 5.91 (s, 1H), 7.05 (s, br, 1H) ppm.

Example X-1-c-1

2,2-Dimethyl-5-oxo-2,5-dihydro-1H-pyrrol-3-yl ethylcarbonate

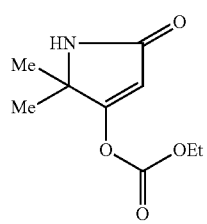

(X-1-c-1)

At 0 to 5° C., a solution of 5.82 g of chloroformic acid ethyl ester in 20 of methylene chloride is added dropwise to a solution of 6.36 g of 5,5-dimethylpyrrolidine-2,4-dione and 5.57 g of triethylamine in 50 ml of methylene chloride. The mixture is then left to reach room temperature over the course of approximately one hour and then stirred for a further 24 hours. The reaction mixture is then diluted with 50 ml of methylene chloride, and extracted by shaking twice with in each case 50 ml of water, twice with in each case 25 ml of 5% strength sodium hydroxide solution and once with 50 ml of saturated aqueous NaCl solution. Drying and concentration by evaporation gives 3.66 g of the title compound in a purity according to HPLC of 98%.

LC/MS: m/e=200 (MH+).

¹H-NMR (400 MHz, CDCl₃): δ=1.31-1.35 (m, 9H), 4.25-4.30 (q, 2H), 5.88 (s, 1H), 7.29 (s, br, 1H) ppm.

Example XVIII-1

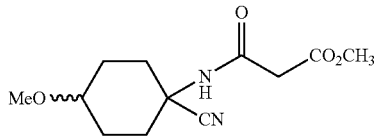 [SMILES: COC(=O)CC(=O)NC1(C#N)CCC(OC)CC1]

5.72 g (30 mmol) of 1-amino-4-methoxycyclohexanecarbonitrile hydrochloride (cis/trans ca. 1:1) are introduced as initial charge in 60 ml of tetrahydrofuran (THF) and admixed with 8.36 ml (60 mmol) of triethylamine and 10 mg of Steglich base. At 0°-10° C., 4.1 g (30 mmol) of malonic acid methyl ester chloride in 5 ml of THF are added dropwise and the mixture is after-stirred for 4 h at room temperature, followed by filtration with suction, after-washing with THF and evaporation in vacuo. The residue is purified by flash column chromatography over silica gel with cyclohexane/ethyl acetate 2:1. This gives 4.96 g (65% of theory) of a cis/trans isomer mixture in the ratio of ca. 7:3.

¹H-NMR (400 MHz, d₆-DMSO): δ=1.41-1.47 (m, 2H), 1.68-1.74 (m, 2H), 1.91-1.99 (m, 2H), 2.21-2.25 (m, 2H), 3.21, 3.24 (2s, trans/cis, tog. 3H, OCH₃), 3.22-3.27 (m, 1H, CHOCH₃), 3.32 (s, 2H, CH₂CO₂CH₃), 3.63 (s, 3H, CO₂CH₃), 8.56, 8.63 (2s, br, trans/cis, tog. 1H, NH) ppm.

Example XX-1

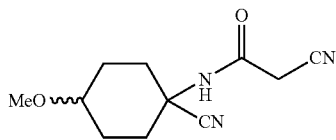 [SMILES: COC1CCC(C#N)(NC(=O)CC#N)CC1]

9.53 g (50 mmol) of 1-amino-4-methoxy-cyclohexanecarbonitrile x HCl (cis/trans mixture ca. 1:1) and 4.25 g (50 mmol) of cyanoacetic acid are introduced as initial charge in 25 ml of pyridine. Then, without cooling, 5.1 g (50 mmol) of acetone hydride in 25 ml of pyridine are added dropwise and, following the addition, the mixture is worked-up immediately. The pyridine is evaporated off in vacuo, and the residue is taken up 2× with in each case 20 ml of toluene and evaporated again. Water is then added, and the mixture is extracted with methylene chloride, followed by drying and evaporation. The residue is pre-purified by flash chromatography over silica gel with ethyl acetate/methanol gradient 9:1 to 4:1. This gives 6.86 g of a wax which smells strongly of vinegar; this is recrystallized from 50 ml of ethyl acetate. Filtration with suction gives 1.61 g (14.6% of theory) of a white powder.

¹H-NMR (400 MHz, d₆-DMSO): δ=1.37-1.46 (m, 2H), 1.67-1.72 (cm, 2H), 1.91-1.94 (m, 2H), 2.22-2.26 (m, 2H), 3.24 (s, 3H, OCH₃) 3.22-3.26 (m, 1H, CHOCH₃), 3.74 (s, 2H, CO—CH₂CN), 8.81 (s, br, 1H, NH) ppm.

We claim:

1. A process for the preparation of a compound of formula (I)

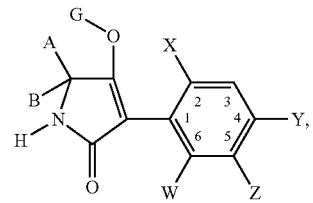

in which

W is hydrogen,

X is methyl,

Y and Z, independently of one another, are hydrogen, alkyl, alkenyl, alkynyl, halogen, cyano, optionally substituted cycloalkyl, alkoxy, haloalkyl, haloalkoxy or in each case optionally substituted aryl or hetaryl, A is hydrogen, is in each case optionally halogen-substituted alkyl, alkenyl, alkoxyalkyl, alkylthioalkyl, saturated or unsaturated, optionally substituted cycloalkyl, in which optionally at least one ring atom is replaced by a heteroatom, or aryl, arylalkyl or hetaryl each of which is optionally substituted by halogen, alkyl, haloalkyl, alkoxy, haloalkoxy, cyano or nitro, B is hydrogen, alkyl or alkoxyalkyl, or A and B, together with the carbon atom to which they are bonded are a saturated or unsaturated unsubstituted or substituted cycle optionally containing at least one heteroatom, G is hydrogen (a) or is one of the groups

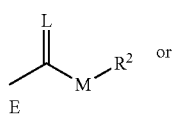

in which

E is a metal ion or an ammonium ion,

L is oxygen or sulphur,

M is oxygen or sulphur,

R¹ is alkyl, alkenyl, alkoxyalkyl, alkylthioalkyl or polyalkoxyalkyl each of which is optionally substituted by halogen or cyano, or is cycloalkyl or heterocyclyl each of which is optionally substituted by halogen, alkyl or alkoxy, or is in each case optionally substituted phenyl, phenylalkyl, hetaryl, phenoxyalkyl or hetaryloxyalkyl, R² is alkyl, alkenyl, alkoxyalkyl or polyalkoxyalkyl each of which is optionally substituted by halogen or cyano, or is in each case optionally substituted cycloalkyl, phenyl or benzyl, comprising reacting a compound of formula (X)

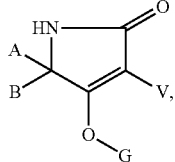
(X)

in which
A and B have the meanings given above,
G is the groups a), b), c) and E given above,
V is hydrogen or
V is $COOR^8$,
where $R^8$ is alkyl
with a compound of formula (XI)

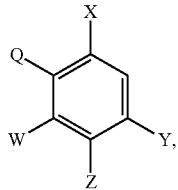
(XI)

in which
W, X, Y and Z have the meanings given above, with the exception that the halogen can now only be fluorine and chlorine, and
Q is triflate, bromine or iodine,
in the presence of a base, a palladium catalyst and a phosphine ligand of the formula (XII')

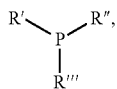
(XII')

in which the radicals
R', R" and R'" independently of one another are $C_1$-$C_{12}$-alkyl, $C_5$-$C_{10}$-cycloalkyl, $C_6$-$C_{10}$-aryl, optionally mono- or polysubstituted by $C_1$-$C_6$-alkyl, $C_1$-$C_6$-alkoxy, $C_1$-$C_6$-alkylamino, $C_1$-$C_6$-dialkylamino or phenyl optionally mono- or polysubstituted by $C_1$-$C_6$-alkyl, $C_1$-$C_6$-alkoxy, $C_1$-$C_6$-alkylamino or $C_1$-$C_6$-dialkylamino,
in a diluent.

2. The process according to claim 1, wherein
W is hydrogen,
X is methyl,
Y and Z are, independently of one another, hydrogen, cyano, fluorine, chlorine, bromine, iodine, $C_1$-$C_4$-alkyl, $C_2$-$C_4$-alkenyl, $C_2$-$C_4$-alkynyl, $C_3$-$C_6$-cycloalkyl optionally monosubstituted by methyl, ethyl, methoxy, fluorine, chlorine, trifluoromethyl or cyclopropyl, $C_1$-$C_6$-alkoxy, $C_1$-$C_4$-haloalkyl, $C_1$-$C_4$-haloalkoxy, or is one of the hetaryl radicals,

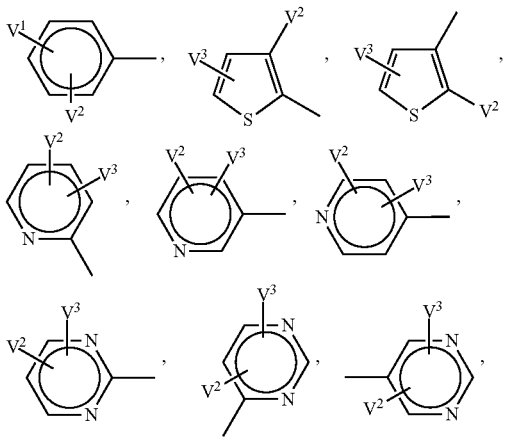

where in the case of (Het)-aryl only one of the radicals Y or Z is hetaryl,
$V^1$ is hydrogen, fluorine, chlorine, bromine, $C_1$-$C_6$-alkyl, $C_1$-$C_4$-alkoxy, $C_1$-$C_2$-haloalkyl, $C_1$-$C_2$-haloalkoxy, nitro, cyano or phenyl optionally mono- to disubstituted by fluorine, chlorine, bromine, $C_1$-$C_4$-alkyl, $C_1$-$C_4$-alkoxy, $C_1$-$C_2$-haloalkyl, $C_1$-$C_2$-haloalkoxy, nitro or cyano, and
$V^2$ and $V^3$ are, independently of one another, hydrogen, fluorine, chlorine, bromine, $C_1$-$C_4$-alkyl, $C_1$-$C_4$-alkoxy, $C_1$-$C_2$-haloalkyl or $C_1$-$C_2$-haloalkoxy.

3. The process according to claim 1, wherein
W is hydrogen,
X is methyl,
Y and Z are, independently of one another, hydrogen, fluorine, chlorine, bromine, iodine, methyl, ethyl, cyclopropyl, methoxy, trifluoromethyl, trifluoromethoxy or a phenyl radical,

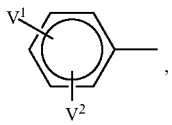

where in the case of phenyl, only one of the radicals Y or Z is phenyl,
$V^1$ is hydrogen, fluorine or chlorine,
$V^2$ is hydrogen, fluorine, chlorine, methyl, ethyl, n-propyl, isopropyl, methoxy, ethoxy or trifluoromethyl,
A is hydrogen, $C_1$-$C_4$-alkyl or $C_1$-$C_2$-alkoxy-$C_1$-$C_2$-alkyl each of which is optionally mono- to trisubstituted by fluorine, or is cyclopropyl, cyclopentyl or cyclohexyl,
B is hydrogen, methyl or ethyl or
A, B and the carbon atom to which they are bonded are saturated $C_5$-$C_6$ cycloalkyl in which optionally one ring member is replaced by nitrogen, oxygen or sulphur and which is optionally mono- or disubstituted by fluorine, chlorine, methyl, ethyl, methoxymethyl, ethoxymethyl, methoxyethyl, ethoxyethyl, trifluoromethyl, methoxy, ethoxy, prop oxy, butoxy, methoxyethoxy, ethoxyethoxy, allyloxy, trifluoroethoxy or cyclopropylmethoxy, where the fluorine, chlorine and trifluoromethyl are not substituents for nitrogen,
A, B and the carbon atom to which they are bonded are $C_6$-cycloalkyl which is optionally substituted by an alkylidenediyl group optionally interrupted by an oxygen atom, or by an alkylidenediyl group containing two non-directly adjacent oxygen atoms, where a 5- or 6-ring ketal is formed and which in each case is optionally mono- or disubstituted by methyl, or A, B and the carbon atom to which they are bonded are $C_5$-$C_6$-cycloalkyl or $C_5$-$C_6$-cycloalkenyl, in which two substituents, together with the carbon atoms to which they are bonded, are $C_2$-$C_4$-alkanediyl or $C_2$-$C_4$-alkenediyl or butadienediyl, G is hydrogen (a) or one of the groups

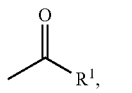
(b)

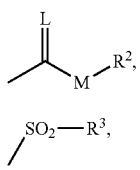
(c)

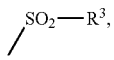
(d)

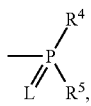
(e)

E, or
(f)

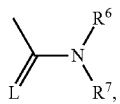
(g)

in which

E is a metal ion or an ammonium ion,

L is oxygen or sulphur,

M is oxygen or sulphur, $R^1$ is $C_1$-$C_{10}$-alkyl, $C_2$-$C_{10}$-alkenyl, $C_1$-$C_4$-alkoxy-$C_1$-$C_2$-alkyl, $C_1$-$C_4$-alkylthio-$C_1$-$C_2$-alkyl each of which is optionally mono- to trisubstituted by fluorine or chlorine, or is $C_3$-$C_6$-cycloalkyl optionally monosubstituted by fluorine, chlorine, methyl, ethyl or methoxy, or is phenyl optionally mono- to disubstituted by fluorine, chlorine, bromine, cyano, nitro, methyl, ethyl, n-propyl, isopropyl, methoxy, ethoxy, trifluoromethyl or trifluoromethoxy, or is furanyl, thienyl or pyridyl each of which is optionally monosubstituted by chlorine, bromine or methyl, $R^2$ is $C_1$-$C_{10}$-alkyl, $C_2$-$C_{10}$-alkenyl or $C_1$-$C_4$-alkoxy-$C_2$-$C_4$-alkyl each of which is optionally mono- to trisubstituted by fluorine or chlorine, or is cyclopentyl or cyclohexyl or is phenyl or benzyl each of which is optionally mono- to disubstituted by fluorine, chlorine, cyano, nitro, methyl, ethyl, methoxy, trifluoromethyl or trifluoromethoxy, $R^3$ is methyl, ethyl, propyl or isopropyl each of which is optionally mono- to trisubstituted by fluorine or chlorine, or phenyl in each case optionally monosubtituted by fluorine, chlorine, bromine, methyl, ethyl, isopropyl, tert-butyl, methoxy, ethoxy, isopropoxy, trifluoromethyl, trifluoromethoxy, cyano or nitro, $R^4$ and $R^5$, independently of one another, are $C_1$-$C_4$-alkoxy or $C_1$-$C_4$-alkythio, or are phenyl, phenoxy or phenylthio each of which is optionally monosubstituted by fluorine, chlorine, bromine, nitro, cyano, methyl, methoxy, trifluoromethyl or trifluoromethoxy, and $R^6$ and $R^7$, independently of one another, are hydrogen, $C_1$-$C_4$-alkyl, $C_3$-$C_6$-cycloalkyl, $C_1$-$C_4$-alkoxy, $C_3$-$C_4$-alkenyl or $C_1$-$C_4$-alkoxy-$C_2$-$C_4$-alkyl, phenyl optionally mono- to disubstituted by fluorine, chlorine, bromine, methyl, methoxy or trifluoromethyl, or together are a $C_5$-$C_6$-alkylene radical in which optionally one methylene group is replaced by oxygen or sulphur.

4. The process according to claim 1, wherein

W is hydrogen,

X is methyl,

Y and Z are, independently of one another, hydrogen, chlorine, methyl or the radical

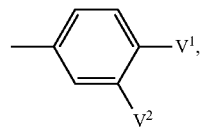

where in this case only one of the radicals Y or Z is

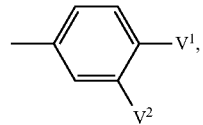

$V^1$ is hydrogen, fluorine or chlorine, $V^2$ is hydrogen, fluorine or chlorine, A is methyl, ethyl, propyl, isopropyl or cyclopropyl, B is hydrogen or methyl, A, B and the carbon atom to which they are bonded are saturated $C_5$-$C_6$-cycloalkyl in which optionally one ring member is replaced by oxygen and which is optionally monosubstituted by fluorine, chlorine, methyl, ethyl, methoxymethyl, methoxy, ethoxy, propoxy, butoxy, or trifluoroethoxy, or A, B and the carbon atom to which they are bonded are $C_6$-cycloalkyl which is optionally substituted by an alkylidenediyl group optionally interrupted by a oxygen, or by an alkylidenediyl group containing two non-directly adjacent oxygen atoms, where a 5- or 6-ring ketal is formed, each of which optionally is mono- or disubstituted by methyl, G is hydrogen (a) or one of the groups

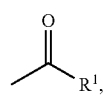
(b)

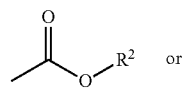
(c)

or

E,
(f)

in which

E is a lithium, sodium, potassium, rubidium, caesium, magnesium, calcium ion or an ammonium ion, $R^1$ is methyl, ethyl, propyl, isopropyl, butyl, isobutyl, sec-butyl, tert-butyl, cyclopropyl, cyclopentyl or cyclohexyl, and $R^2$ is methyl, ethyl, propyl, isopropyl, butyl, isobutyl, sec-butyl, tert-butyl, or benzyl.

5. The process according to claim 1, wherein the reaction temperature is between 50° C. and 180° C.

* * * * *